US012566179B2

(12) United States Patent
Ahmed et al.

(10) Patent No.: US 12,566,179 B2
(45) Date of Patent: Mar. 3, 2026

(54) CORONAVIRUS ASSAYS, DIAGNOSTIC METHODS, TREATMENT METHODS, AND COMPOSITIONS RELATED THERETO

(71) Applicant: Emory University, Atlanta, GA (US)

(72) Inventors: Rafi Ahmed, Decatur, GA (US); Mehul Suthar, Atlanta, GA (US); Jens Wrammert, Atlanta, GA (US); John Roback, Atlanta, GA (US); Robert Kauffman, Atlanta, GA (US)

(73) Assignee: Emory University, Atlanta, GA (US)

( * ) Notice: Subject to any disclaimer, the term of this patent is extended or adjusted under 35 U.S.C. 154(b) by 788 days.

(21) Appl. No.: 17/922,670

(22) PCT Filed: May 3, 2021

(86) PCT No.: PCT/US2021/030461
§ 371 (c)(1),
(2) Date: Nov. 1, 2022

(87) PCT Pub. No.: WO2021/222890
PCT Pub. Date: Nov. 4, 2021

(65) Prior Publication Data
US 2023/0266336 A1 Aug. 24, 2023

Related U.S. Application Data

(60) Provisional application No. 63/142,461, filed on Jan. 27, 2021, provisional application No. 63/019,177, filed on May 1, 2020.

(51) Int. Cl.
*G01N 33/68* (2006.01)
*G01N 33/543* (2006.01)
*G01N 33/569* (2006.01)

(52) U.S. Cl.
CPC ... *G01N 33/6854* (2013.01); *G01N 33/54386* (2013.01); *G01N 33/56983* (2013.01); *G01N 2333/165* (2013.01)

(58) Field of Classification Search
CPC ......................... A61K 39/12; G01N 2333/165
See application file for complete search history.

(56) References Cited

U.S. PATENT DOCUMENTS 11,112,412 B1 9/2021 Wang

FOREIGN PATENT DOCUMENTS

| WO | 2007044695 | 4/2007 |
| WO | 2015057666 | 4/2015 |
| WO | 2016170484 | 10/2016 |

OTHER PUBLICATIONS

Amanat et al. A serological assay to detect SARS-CoV-2 seroconversion in humans, Nature Medicine vol. 26, pp. 1033-1036 (2020).
Andersen et al. The proximal origin of SARS-CoV-2, Nature Medicine vol. 26, pp. 450-452 (2020).
Suthar et al. Rapid Generation of Neutralizing Antibody Responses in COVID-19 Patients, 2020, Cell Reports Medicine 1, 100040.
Walls et al. Structure, Function, and Antigenicity of the SARSCoV-2 Spike Glycoprotein, 2020, Cell 180, 281-292.
Yan et al. Structural basis for the recognition of SARS-CoV-2 by full-length human ACE2, Science, 367, 1444-1448 (2020).
Zuo et al. Expression and puriWcation of SARS coronavirus proteins using SUMO-fusions, Protein Expression and Purification 42 (2005) 100-110.

*Primary Examiner* — Bao Q Li
(74) *Attorney, Agent, or Firm* — Emory Patent Group

(57) ABSTRACT

This disclosure relates to coronavirus assays, diagnostic methods, treatment methods, and compositions related thereto. In certain embodiments, this disclosure relates to ACE2 receptor binding domain peptides and uses in serological assays and vaccination methods.

12 Claims, 4 Drawing Sheets

Specification includes a Sequence Listing.

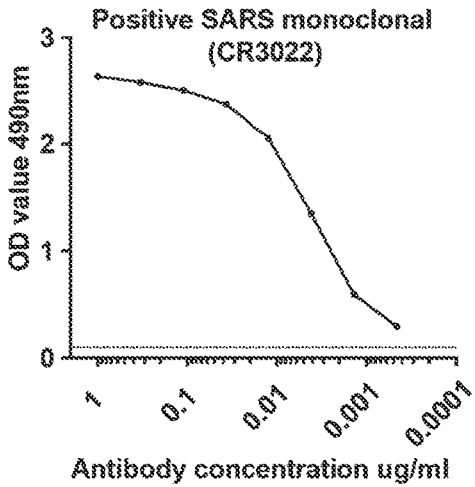
FIG. 1A
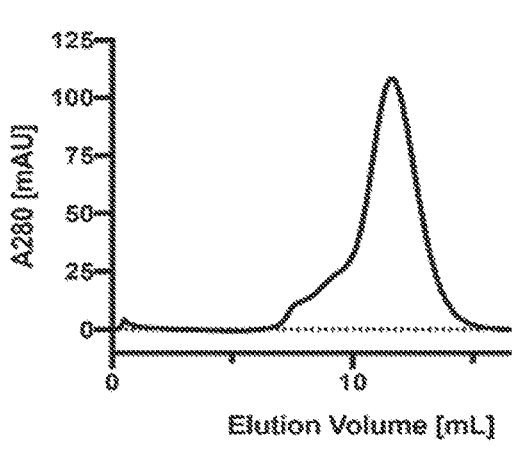
FIG. 1B
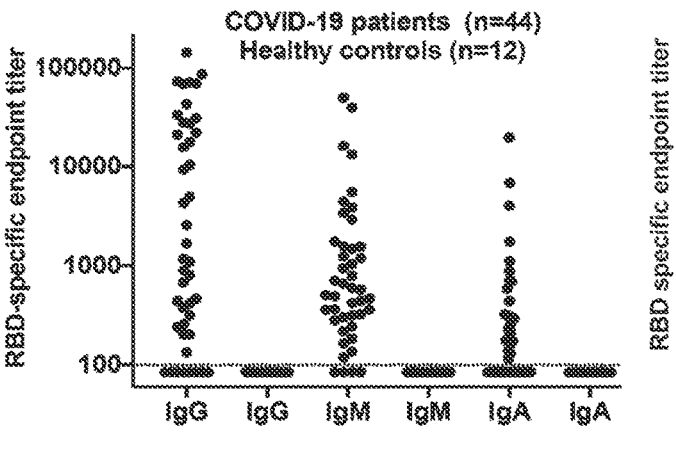
FIG. 1C
FIG. 1D

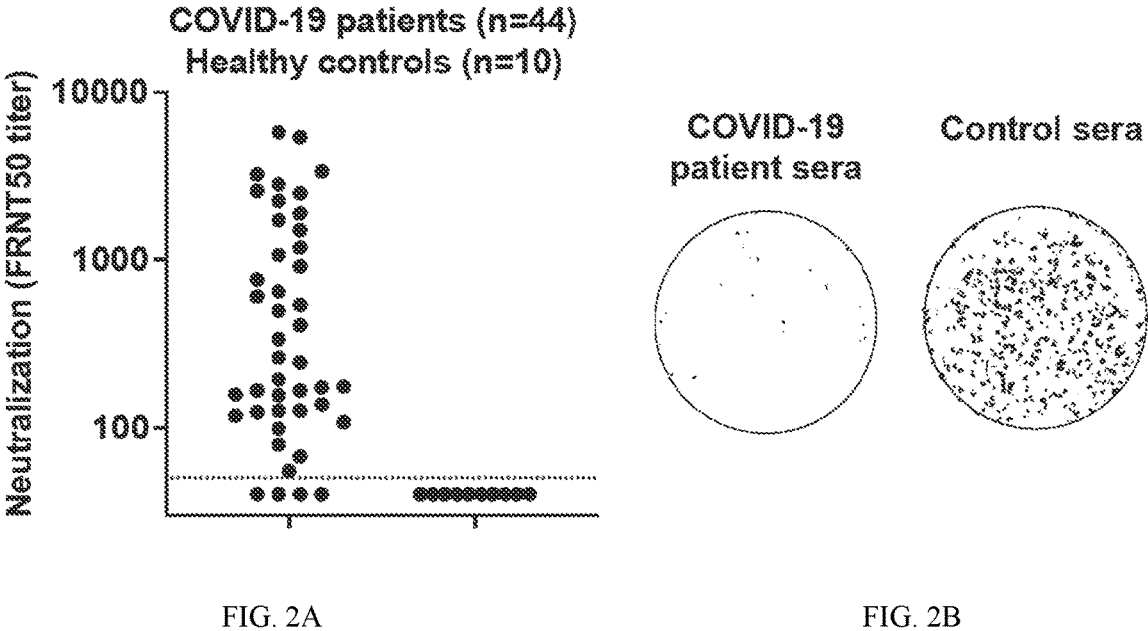
FIG. 2A                                                            FIG. 2B
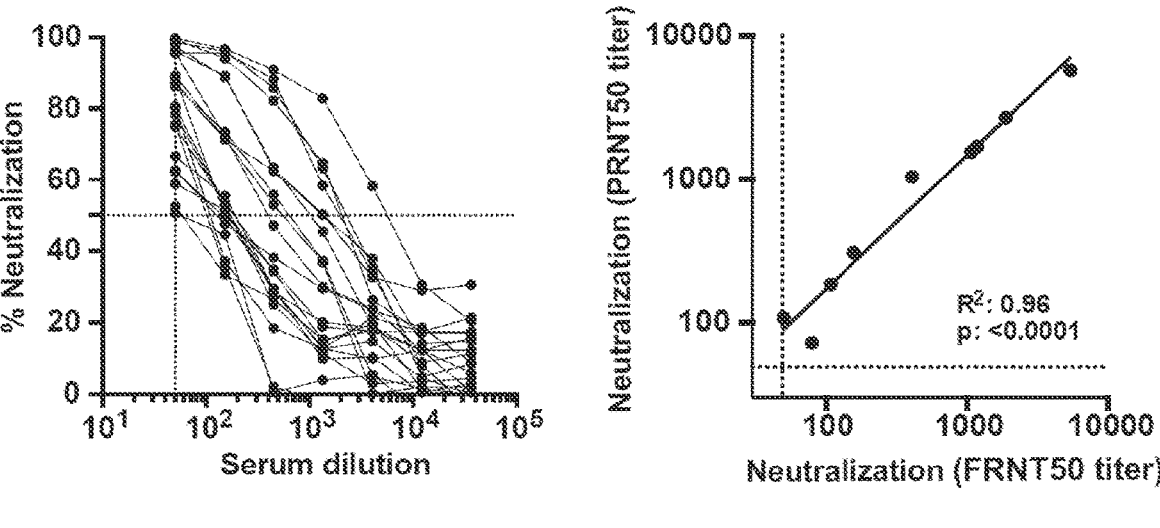
FIG. 2C                                                            FIG. 2D

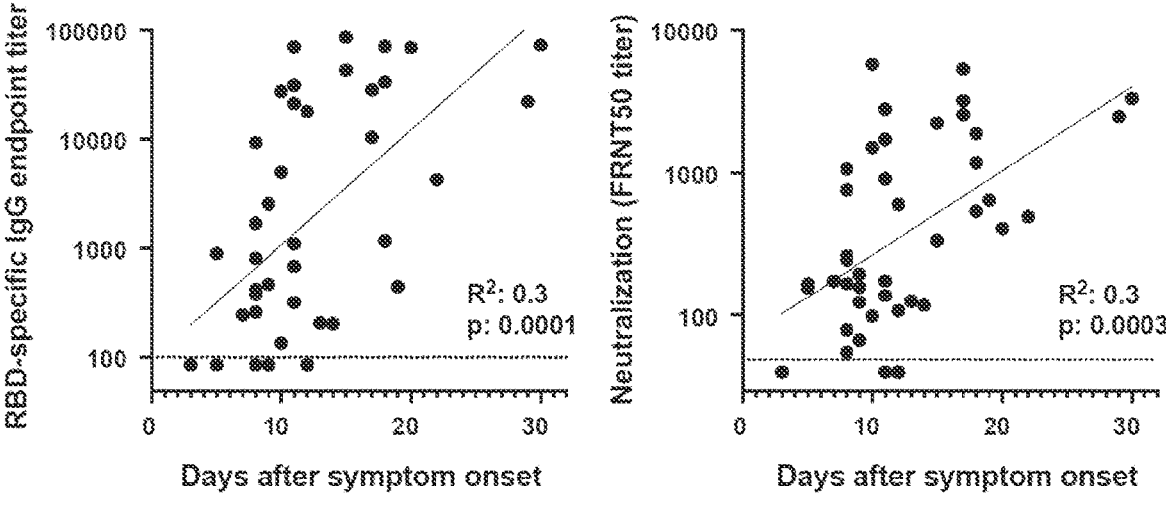
FIG. 3A                                                    FIG. 3B
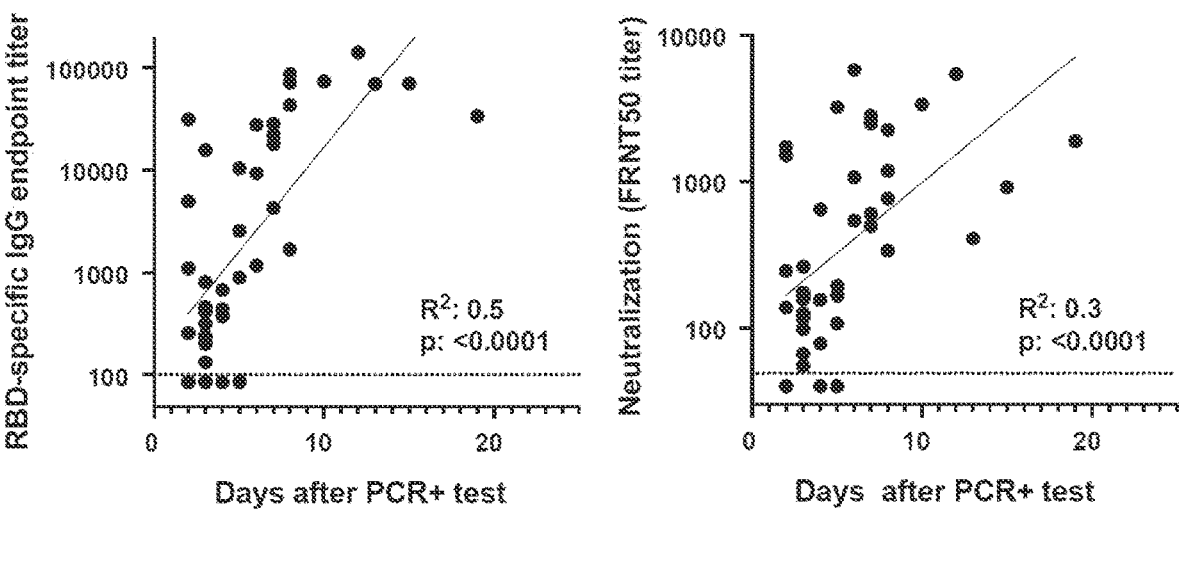
FIG. 3C                                                    FIG. 3D

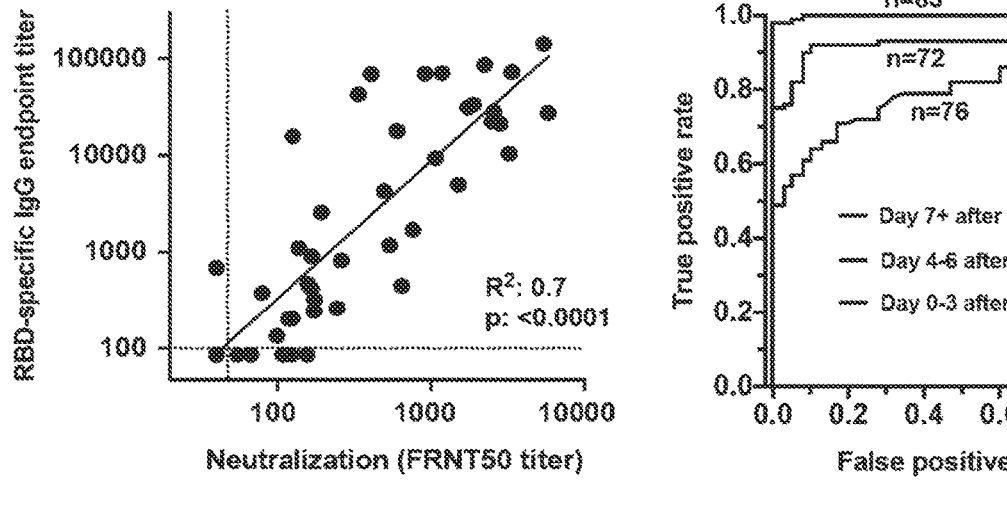
FIG. 4A                                    FIG. 4B

CORONAVIRUS ASSAYS, DIAGNOSTIC METHODS, TREATMENT METHODS, AND COMPOSITIONS RELATED THERETO

CROSS-REFERENCE TO RELATED APPLICATIONS

This application is the National Stage of International Application No. PCT/US2021/030461 filed May 3, 2021, which claims the benefit of U.S. Provisional Application No. 63/019,177 filed May 1, 2020 and U.S. Provisional Application No. 63/142,461 filed Jan. 27, 2021. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 20171PCT_ST25.txt. The text file is 30 KB, was created on Apr. 30, 2021, and is being submitted electronically via EFS-Web.

BACKGROUND

Some common colds are due to certain coronavirus (CoV) strains associated with mild symptoms. More dangerous human strains such as severe acute respiratory syndrome associated coronavirus (SARS-CoV-1) and SARS-CoV-2 (also referred to as COVID-19) are believed to result from coronavirus strains jumping to humans by secondary zoonotic transfers, e.g., from bats to cats and cats to humans. In humans, SARS-CoV-2 can be transferred from individuals who have mild symptoms or are asymptomatic and has caused numerous deaths worldwide. Thus, there is a need to identify treatments and preventative measures.

Walls et al. report that the SARS-CoV-2 spike protein is involved in viral cell entry by recognizing human angiotensin converting enzyme 2 (ACE2). Cell, 2020, 180, 1-12.

Andersen et al. report six receptor binding domain amino acids L455, F486, Q493, S494, N501 and Y505 are involved in binding to ACE2 receptors in SARS-CoV-2. Nat Med, 2020.

Baric et al. report methods and compositions for coronavirus diagnostics and therapeutics. WO2015057666A1.

References cited herein are not an admission of prior art.

SUMMARY

This disclosure relates to coronavirus assays, diagnostic methods, treatment methods, and compositions related thereto. In certain embodiments, this disclosure relates to ACE2 receptor binding domain peptides and uses in serological assays and vaccination methods.

In certain embodiments, this disclosure relates to peptides, labeled peptides, and fusion peptides disclosed herein comprising or consisting of sequences or variants disclosed herein. In certain embodiments, this disclosure relates to solid surfaces and particles coated with or conjugated to peptides, fusion peptides, or variants disclosed herein.

In certain embodiments, this disclosure relates to peptides comprising or consisting of SEQ

```
                                    SEQ ID NO: 1
(MFVFLVLLPLVSRVQPTESIVRFPNITNLCPFGEVENATRFASVYAWN

RKRISNCVADYSVLYNSASFSTFKCYGVSPTKLNDLCFTNVYADSFVIR

GDEVRQIAPGQTGKIADYNYKLPDDFTGCVIAWNSNNLDSKVGGNYNYL

YRLFRKSNLKPFERDISTEIYQAGSTPCNGVEGFNCYFPLQSYGFQPTN

GVGYQPYRVVVLSFELLHAPATVCGPKKSTNLVKNKCVNF) or
``` variant thereof. In certain embodiments, this disclosure relates to fusion peptides comprising SEQ ID NO: 1. In certain embodiments, the peptide contains a polyhistidine on the C-terminus of SEQ ID NO: 1 separated by a polypeptide linker. In certain embodiments, the peptide contains a polyglycine linker and a polyhistidine on the C-terminus of SEQ ID NO: 1. In certain embodiments, the peptide has a serine amino acid between the polyglycine linker and the polyhistidine.

In certain embodiments, this disclosure relates to peptides comprising or consisting of SEQ

```
                                    SEQ ID NO: 2
(MFVFLVLLPLVSRVQPTESIVRFPNITNLCPFGEVENATRFASVYAWN

RKRISNCVADYSVLYNSASFSTFKCYGVSPTKLNDLCFTNVYADSFVIR

GDEVRQIAPGQTGKIADYNYKLPDDFTGCVIAWNSNNLDSKVGGNYNYL

YRLFRKSNLKPFERDISTEIYQAGSTPCNGVEGFNCYFPLQSYGFQPTN

GVGYQPYRVVVLSFELLHAPATVCGPKKSTNLVKNKCVNFGGGGSHHHH

HH).
```

In certain embodiments, a peptide disclosed herein is conjugated to or coated on a solid surface, a particle, magnetic particle, or a fluorescent particle. In certain embodiments, a peptide disclosed herein is conjugated to a fluorescent dye, radioisotope, or enzymatic label.

In certain embodiment, this disclosure relates to nucleic acids and vectors encoding peptides disclosed herein in operable combination with promoters, e.g., heterologous promotors. In certain embodiments, this disclosure relates to expression systems or cells comprising nucleic acids and vectors disclosed herein.

In certain embodiments, this disclosure relates to methods of analyzing coronavirus antibody production and specific antibody responses in subjects at risk of, diagnosed with, or exhibiting symptoms of a coronavirus infection. In certain embodiments, this disclosure relates to methods of detecting antibodies specific for a coronavirus receptor binding domain in a blood product of a subject using an enzyme-linked immunosorbent assay, plaque forming assay, or a focus reduction neutralization assay.

In certain embodiments, this disclosure relates to methods of detecting the presence of a coronavirus in a sample comprising: contacting a sample with a peptide disclosed herein under conditions whereby an peptide/antibody complex can form; and detecting formation of an peptide/antibody complex, whereby detection of formation of the peptide/antibody complex detects a coronavirus in the sample.

In certain embodiments, this disclosure relates to methods of producing antibodies comprising administering a peptide disclosed herein to a subject in an effective amount to result in the production of peptide specific antibodies. In certain embodiments, methods further comprise isolating the peptide specific antibodies or peptide specific antibody producing cells from the subject.

In certain embodiments, this disclosure relates to methods of detecting coronavirus antibodies in a sample obtained from a subject known or suspected to be infected with a coronavirus comprising contacting a sample from a subject containing a coronavirus antibody that specifically binds an ACE2 receptor binding domain with a peptide as disclosed herein; and detecting binding of the antibody to the peptide thereby detecting a coronavirus antibody in the sample of the subject.

In certain embodiments, this disclosure relates to methods of detecting a coronavirus antibody comprising providing a solid surface coated with a peptide disclosed herein; contacting the solid surface with a sample obtained from a subject known or suspected to be infected with a coronavirus; wherein if the sample comprises an antibody that binds an expose epitope of the peptide, then a complex of the peptide and subject derived antibody is formed; contacting the complex with an immunoglobulin specific antibody conjugated to a label providing a second complex of the labeled immunoglobulin specific antibody and the subject derived antibody; detecting the second complex of a labeled immunoglobulin specific antibody and the subject derived antibody thereby detecting a coronavirus antibody in the sample of the subject.

In certain embodiments, this disclosure relates to methods of measuring or quantifying whether a subject has neutralizing antibodies to a coronavirus infection comprising obtaining a blood sample obtained from a subject known or suspected to be infected with a coronavirus; contacting the sample with cells containing surface expression of ACE2 and an infectious coronavirus; culturing the cells; and measuring and/or quantifying infected foci or plaque compared to a reference value or normalized value, wherein if the sample comprises neutralizing antibodies, then coronavirus infection of the cells will be prevented or infection will be reduced providing minimal change, or substantially unaltered viability, or growth of the cultured cells, and wherein if the sample does not comprise neutralizing antibodies, then infectious coronavirus will infect and alter the cultured cells (in a similar manner to what would be observed by exposing the cells to coronavirus without exposure to the sample).

In certain embodiments, this disclosure relates to treating a subject with a blood product from a coronavirus recovered patient which contains neutralizing antibodies identified by methods disclosed herein.

In certain embodiments, this disclosure relates to methods of treating a coronavirus infection comprising administering to a subject in need thereof an effective amount of a blood product from a patient that has recovered from a prior coronavirus infection; wherein a sample of the patient is measured for IgG and IgA providing measured levels of IgG and IgA; or wherein a sample of the patient is measured for IgG and IgM providing measured levels of IgG and IgM; wherein the blood product is selected from a patient wherein the measured levels of IgM are lower as compared to IgG; or wherein the blood product is selected from a patient wherein the measured levels of IgA are lower as compared to IgG. In certain embodiments, the subject is known or suspected to be infected with a coronavirus. In certain embodiments, the subject is diagnosed with respiratory distress syndrome. In certain embodiments, the blood product is plasma or whole blood.

In certain embodiments, this disclosure relates to methods of determining immunization efficiency to a vaccine for a coronavirus that causes respiratory distress syndrome comprising administering a vaccine for a coronavirus to a subject; measuring IgG and IgM in a sample of the subject providing measured levels of IgG and IgM; or measuring IgG and IgA in a sample of the subject providing measured levels of IgG and IgA; diagnosing the subject as having an effective immunization if the measured levels of IgM are lower as compared to IgG; or diagnosing the subject as having an effective immunization if the measured levels of IgA are lower as compared to IgG.

In certain embodiments, this disclosure relates to pharmaceutical compositions comprising a peptide disclosed herein and a pharmaceutically acceptable excipient.

In certain embodiments, this disclosure relates to vaccination methods comprising administering an effective amount of a peptide as disclosed herein to a subject optionally in combination with an adjuvant.

BRIEF DESCRIPTION OF THE SEVERAL VIEWS OF THE DRAWINGS

FIG. 1A shows data on ELISA validation of the RBD protein using a monoclonal antibody (CR3022) directed against the spike protein RBD.

FIG. 1B shows data from size exclusion chromatography of the recombinant RBD protein by elution profile (UV absorption 280 nm) of 1 mg RBD protein analyzed in PBS buffer on a Superdex™ 75 (10/300) size exclusion column.

FIG. 1C shows ELISA endpoint titers for SARS-CoV-2 RBD specific IgG, IgA and IgM in PCR confirmed acute COVID-19 patients (n=44) and healthy controls collected in early 2019. Endpoint cutoff values were calculated using the mean of the 12 healthy controls at 1/100 dilution, times 3 standard deviations (shown as a dotted line).

FIG. 1D shows representative ELISA assays for 10 patients and 12 healthy controls.

FIG. 2A shows data indicating COVID-19 patient plasma neutralizes SARS-CoV-2 due to neutralization activity of serum samples against SARS-CoV-2. The FRNT50 titers of COVID-19 patients (n=44) and healthy controls (n=10) sera were determined by a FRNT assay using an immunological stain to detect infected foci. Each circle represents one serum sample. The dotted line represents the maximum concentrations of the serum tested (1/50).

FIG. 2B shows a representative sample showing reduction in foci from a neutralization assay with sera from an infected COVID-19 patient.

FIG. 2C shows representative FRNT50 curves (n=22). Dotted line represents the 50% neutralization.

FIG. 2D shows a comparison of PRNT50 against FRNT50 titers (n=9). Each experiment was performed at least twice, and a representative data set is shown.

FIG. 3A shows data on RBD-specific IgG titers with days after symptom onset. Correlation analysis were performed by log transformation of the endpoint ELISA titers followed by linear regression analysis.

FIG. 3B shows neutralization titers days after symptom onset indicating SARS-CoV-2 antibody responses correlate with the progression of acute SARS-CoV-2 infection.

FIG. 3C shows data on RBD-specific IgG titers days after PCR positive confirmation for each patient.

FIG. 3D shows neutralization titers days after PCR positive confirmation for each patient.

FIG. 4A shows a comparison of RBD-specific IgG endpoint titers with SARS-CoV-2-specific FRNT50 titers indicating RBD-specific antibody titers as a surrogate of neutralization potency in acutely infected COVID-19 patients.

Correlation analysis was performed by log transformation of the endpoint ELISA or FRNT50 titers followed by linear regression analysis.

FIG. 4B shows validation data for use of RBD-specific ELISA in high-throughput clinical testing. Sera (n=231) were collected from COVID-19 patients within the first 22 days after PCR-confirmation. Sera (n=40) collected in 2019 were used as negative controls. ROC curves are shown comparing the true positive and false negative rates of the ELISA using different OD cutoffs and sera collected at different times post-infection. Whereas the RBD ELISA produced an area under the curve (AUC) of 0.80 when samples were collected close to the time of infection (within 3 days of positive PCR; n=76), longer sampling times resulted in better performance. Assay performance was nearly perfectly discriminatory (AUC=1.00) when samples were collected at least 7 days after the positive PCR (n=83).

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps.

"Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

A "sample" or "biological sample" can be any biological material, such as a biological fluid, a blood product, an extract from a cell, an extracellular matrix isolated from a cell, a cell (in solution or bound to a solid support), a tissue, a tissue homogenate, and the like as are well known in the art.

As used herein, "blood sample" or "blood product" encompasses a biological sample which is derived from blood obtained from an individual and can be used in a diagnostic or monitoring assay. The definition encompasses whole blood, plasma, and serum.

In certain embodiments, methods disclosed herein may make measurements that are compared to a normal or reference value. As used herein, a "reference value" can be an absolute value; a relative value; an average value; a median value, a mean value, or a value as compared to a particular control or baseline value. A reference value can be based on an individual sample or a large number of samples, such as from patients or normal individuals.

A "normalized measured" value refers to a measurement taken and adjusted to take background into consideration. Background subtraction to obtain total fluorescence is considered a normalized measurement. The background subtraction allows for the correction of background fluorescence that is inherent in the optical system and assay buffers.

"Subject" refers to any animal, preferably a human patient, livestock, rodent, monkey, or domestic pet. The term is used herein to encompasses apparently healthy, non-infected individuals or a patient who is known to be infected with, diagnosed with, a pathogen. In certain embodiments, the subject is a human subject of advanced age or elderly e.g., more than 45, 55, or 65 years old.

In certain embodiments, an "effective amount" in the context of administration of a therapy to a subject refers to the amount of a therapy which is sufficient to achieve one, two, three, four, or more of the following effects: (i) reduce or ameliorate the severity of a viral infection, disease or symptom associated therewith; (ii) reduce the duration of a viral infection, disease or symptom associated therewith; (iii) prevent the progression of a viral infection, disease or symptom associated therewith; (iv) cause regression of a viral infection, disease or symptom associated therewith; (v) prevent the development or onset of a viral infection, disease or symptom associated therewith; (vi) prevent the recurrence of a viral infection, disease or symptom associated therewith; (vii) reduce or prevent the spread of a viral from one cell to another cell, one tissue to another tissue, or one organ to another organ; (viii) prevent or reduce the spread of a viral from one subject to another subject; (ix) reduce organ failure associated with a viral infection; (x) reduce hospitalization of a subject; (xi) reduce hospitalization length; (xii) increase the survival of a subject with a viral infection or disease associated therewith; (xiii) eliminate a viral infection or disease associated therewith; (xiv) inhibit or reduce viral replication; (xv) inhibit or reduce the entry of an virus into a host cell(s); (xvi) inhibit or reduce replication of the virus genome; (xvii) inhibit or reduce synthesis of virus proteins; (xviii) inhibit or reduce assembly of virus particles; (xix) inhibit or reduce release of virus particles from a host cell(s); (xx) reduce virus titer; and/or (xxi) enhance or improve the prophylactic or therapeutic effect(s) of another therapy.

In certain embodiments, the effective amount does not result in complete protection from a coronavirus infection but results in a lower titer or reduced number of viruses compared to an untreated subject with a viral infection. In certain embodiments, the effective amount results in a 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of virus relative to an untreated subject with a viral infection. Benefits of a reduction in the titer, number or total burden of virus include, but are not limited to, less severe symptoms of the infection, fewer symptoms of the infection and a reduction in the length of the disease associated with the infection.

Compositions described herein may be delivered to a subject by a variety of routes. These include, but are not limited to, intranasal, intratracheal, oral, intradermal, intramuscular, intraperitoneal, transdermal, intravenous, conjunctival, and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, immunogenic compositions disclosed herein are administered intradermally. In certain embodiments, this disclosure contemplates administration using a transdermal patch for diffusion of the drug across the skin or by microneedle injection. In certain embodiments, it may be desirable to introduce the pharmaceutical compositions into the lungs by any suitable route. Pulmonary administration can also be employed, e.g., by use of an inhaler or nebulizer, and formulation with an aerosolizing agent for use as a spray.

As used herein, the term "combination with" when used to describe administration with an additional treatment means that the agent may be administered prior to, together with, or after the additional treatment, or a combination thereof.

The terms "protein," "peptide," and "polypeptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit be limited to natural amino acids. The term includes non-naturally occurring amino acids and modifications such as, substitutions, glycosylations, and addition of hydrophilic or lipophilic moieties.

In the context of a fusion or chimeric peptide (a peptide comprising two or more peptide segments), a "heterologous" peptide sequence is a comparative term and refers to a peptide segment that would not naturally occur together with the other segment, e.g., because one the of the segments is derived from a different organism, a label, random, or the segments are derived from the same organism but are not arranged in the same order or way. In certain embodiments, a heterologous fusion peptide of this disclosure may contain a peptide sequence disclosed herein and a fluorescent protein sequence, a protease cleaving sequence, a self-cleaving sequence, a ligand, antibody epitope, or a polyhistidine sequence.

As used herein, the term "conjugated" refers to linking molecular entities through covalent bonds, or by other specific binding interactions, such as due to hydrogen bonding and other van der Walls forces. The force to break a covalent bond is high, e.g., about 1500 pN for a carbon to carbon bond. The force to break a combination of strong protein interactions is typically a magnitude less, e.g., biotin to streptavidin is about 150 pN. Thus, a skilled artisan would understand that conjugation must be strong enough to bind molecular entities in order to implement the intended results.

A "linking group" refers to any variety of molecular arrangements that can be used to bridge to molecular moieties together, e.g., a peptide bridge. An example formula are chemical chains of —$R_n$— wherein R is selected individually and independently at each occurrence as:

—$CR_nR_n$—, —$CHR_n$—, —CH—, —C—, —$CH_2$—, —$C(OH)R_n$, —C(OH)(OH)—, —C(OH)H, —$C(Hal)R_n$—, —C(Hal)(Hal)-, —C(Hal)H—, —$C(CN)R_n$—, —C(CN)(CN)—, —C(CN)H—, —O—, —S—, —N—, —NH—, —$NR_n$—, —(C—O)—, —(C=NH)—, —(C=S)—, —(C=CH)—, which may contain single, double, or triple bonds individually and independently between the R groups. If an R is branched with an $R_n$ it may be terminated with a group such as —$CH_3$, —H, —CH—$CH_2$, —CCH, —OH, —SH, —$NH_2$, —$N_3$, —CN, or -Hal, or two branched Rs may form an aromatic or non-aromatic cyclic structure. It is contemplated that in certain instances, the total Rs or "n" may be less than 100 or 50 or 25 or 10. It is contemplated that in certain instances, each $R_n$ may be individually and independently an integer selected from 1, 2, 3, 4, 5, 6, 7, 8, 9, 10, 11, 12, 13, 14, 15, 15, 17, 18, 19, 20, 21, 22, 23, 24, and 25. Examples of linking groups include bridging alkyl groups and alkoxyalkyl groups.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a peptide "label" refers to incorporation of a heterologous polypeptide in the peptide, wherein the heterologous sequence can be identified by a specific binding agent, e.g., antibody, or bind to a metal such as nickel/nitrilotriacetic acid, e.g., a poly-histidine sequence. Specific binding agents and metals can be conjugated to solid surfaces to facilitate purification methods. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods).

Various methods of labeling polypeptides and glycoproteins are known in the art and may be used. Examples of labels for polypeptides include, but are not limited to, the following: radioisotopes or radionucleotides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels may be attached by spacer arms of various lengths to reduce potential steric hindrance.

The term "specific binding agent" refers to a molecule, such as a proteinaceous molecule, that binds a target molecule with a greater affinity than other random molecules or proteins. Examples of specific binding agents include antibodies that bind an epitope of an antigen or a receptor which binds a ligand. "Specifically binds" refers to the ability of a specific binding agent (such as an ligand, receptor, enzyme, antibody or binding region/fragment thereof) to recognize and bind a target molecule or polypeptide, such that its affinity (as determined by, e.g., affinity ELISA or other assays) is at least 10 times as great, but optionally 50 times as great, 100, 250 or 500 times as great, or even at least 1000 times as great as the affinity of the same for any other or other random molecule or polypeptide.

In certain contexts, an "antibody" refers to a protein based molecule that is naturally produced by animals in response to the presence of a protein or other molecule or that is not recognized by the animal's immune system to be a "self" molecule, i.e. recognized by the animal to be a foreign molecule and an antigen to the antibody. The immune system of the animal will create an antibody to specifically bind the antigen, and thereby targeting the antigen for elimination or degradation. It is well recognized by skilled artisans that the molecular structure of a natural antibody can be synthesized and altered by laboratory techniques. Recombinant engineering can be used to generate fully synthetic antibodies or fragments thereof providing control over variations of the amino acid sequences of the antibody. Thus, as used herein the term "antibody" is intended to include natural antibodies, monoclonal antibody, or non-naturally produced synthetic antibodies, bispecific antibodies, and binding fragments thereof, such as single chain binding fragments. These antibodies may have chemical modifications. The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same antigen. The term "monoclonal" is not limited to any particular method for making the antibody, nor is the term limited to antibodies produced in a particular species, e.g., mouse, rat, etc.

From a structural standpoint, an antibody is a combination of proteins: two heavy chain proteins and two light chain proteins. The heavy chains are longer than the light chains. The two heavy chains typically have the same amino acid sequence. The heavy chain contains an extra C-terminal peptide chain (Fc fragment) defining the antibody as a specific class, e.g., IgG, IgA, IgM, IgD, or IgE. Similarly, the two light chains typically have the same amino acid sequence. Each of the heavy and light chains contain N-terminal variable segments that contains amino acid sequences which participate in binding to the antigen. The variable segments of the heavy chain do not have the same amino acid sequences as the light chains. The variable segments are often referred to as the antigen binding domains. The antigen and the variable regions of the antibody may physically interact with each other at specific smaller segments of an antigen often referred to as the "epitope." Epitopes usually consist of surface groupings of molecules, for example, amino acids or carbohydrates. The terms "variable region," "antigen binding domain," and "antigen binding region" refer to that portion of the antibody molecule which contains the amino acid residues that interact with an antigen and confer on the antibody its specificity and affinity for the antigen. Small binding regions within the antigen-binding domain that typically interact with the epitope are also commonly alternatively referred to as the "complementarity-determining regions, or CDRs."

In certain embodiments, this disclosure contemplates that peptides disclosed herein may be variants. Variants may include 1 or 2 or more amino acid substitutions or conserved substitutions. Variants may include 3 or 4 or more amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants include any peptide disclosed herein with greater than 80%, 89%, 90%, 95%, 98%, or 99% identity or similarity.

Variant peptides can be produced by mutating a vector to produce appropriate codon alternatives for polypeptide translation. Active variants and fragments can be identified with a high probability using computer modeling. Shihab et al. report an online genome tolerance browser. BMC Bioinformatics, 2017, 18 (1): 20. Ng et al. report methods of predicting the effects of amino acid substitutions on protein function. Annu Rev Genomics Hum Genet, 2006, 7:61-80. Teng et al. Approaches and resources for prediction of the effects of non-synonymous single nucleotide polymorphism on protein function and interactions. Curr Pharm Biotechnol, 2008, 9 (2): 123-33.

Desired amino acid substitutions (whether conservative or non-conservative) can be determined by those skilled in the art at the time such substitutions are desired. Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLOS Comput Biol. 2016, 12(3):e1004775; Marks et al. Protein structure from sequence variation, Nat Biotechnol. 2012, 30(11):

US 12,566,179 B2

11

1072-80; Mackenzie et al. Curr Opin Struct Biol, 2017, 44:161-167 Mackenzie et al. Proc Natl Acad Sci USA. 113(47):E7438-E7447 (2016); Joseph et al. J R Soc Interface, 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 9) and GGGGT (SEQ ID NO: 10) have a sequence identity of 4 out of 5 or 80%. For example, the polypeptides GGGPPP (SEQ ID NO: 11) and GGGAPPP (SEQ ID NO: 12) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic-FYW; hydrophobic-A VIL; Charged positive: R K H; Charged negative-D E; Polar-STN Q. The amino acid groups are also considered conserved substitutions.

The term "recombinant" when made in reference to a nucleic acid molecule refers to a nucleic acid molecule which is comprised of segments of nucleic acid joined together by means of molecular biological techniques provided that the entire nucleic acid sequence does not occurring in nature, i.e., there is at least one mutation in the overall sequence such that the entire sequence is not naturally occurring even though separately segments may occurring in nature. The segments may be joined in an altered arrangement such that the entire nucleic acid sequence from start to finish does not naturally occur. The term "recombinant" when made in reference to a protein or a polypeptide refers to a protein molecule that is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In certain embodiments, a vector of this disclosure optionally comprises a gene vector element (nucleic acid) such as a selectable marker region, lac operon, a CMV promoter, a hybrid chicken β-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

A "selectable marker" is a nucleic acid introduced into a vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose: galactose-1-phosphate uridyltransferaseI (galT), feedback-insensitive a subunit of anthranilate synthase (OASAID), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

Protein "expression systems" refer to in vivo and in vitro (cell free) systems. Systems for recombinant protein expression typically utilize cells (somatic) transfected with a DNA expression vector that contains the template. The cells are cultured under conditions such that they translate the desired protein. Expressed proteins are extracted for subsequent purification. In vivo protein expression systems using prokaryotic and eukaryotic cells are well known. Proteins may be recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporate encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38 (13): e141, both hereby incorporated by reference in their entirety.

Coronaviruses

Coronaviruses (CoVs) constitute a group of phylogenetically diverse enveloped viruses that encode large plus strand RNA genomes and replicate efficiently in many mammals. Human CoV (HCoVs-229E, OC43, NL63, and HKU1) infections typically result in mild to severe upper and lower respiratory tract disease. Severe Acute Respiratory Syndrome Coronavirus (SARS-CoV-1) emerged in 2002-2003 causing acute respiratory distress syndrome (ARDS) with significant mortality in aged individuals. Middle Eastern Respiratory Syndrome Coronavirus (MERS-CoV) emerged in the Middle East in April of 2012, manifesting as severe pneumonia, acute respiratory distress syndrome (ARDS) and acute renal failure.

SARS-CoV-2, i.e., COVID-19, has caused a devastating pandemic that has afflicted nearly every country throughout the world. The SARS-CoV-2 genome has about 30 kb that can be directly read by ribosomes with host cells. The RNA forms a ribonucleoprotein complex within virus particles having a viral lipid envelope membrane made up of membrane (M) glycoproteins, trimeric spike (S) glycoproteins and envelope (E) proteins. The trimeric units of the spike protein contain a receptor binding domain (RBD) and a fusion domain that anchors it into lipid membrane.

Peptide Compositions

In certain embodiments this disclosure relates to a peptide comprising or consisting of SEQ

```
                                          SEQ ID NO: 1
(MFVFLVLLPLVSRVQPTESIVRFPNITNLCPFGEVENATRFASVYAWN

RKRISNCVADYSVLYNSASFSTFKCYGVSPTKLNDLCFTNVYADSFVIR

GDEVRQIAPGQTGKIADYNYKLPDDFTGCVIAWNSNNLDSKVGGNYNYL

YRLFRKSNLKPFERDISTEIYQAGSTPCNGVEGFNCYFPLQSYGFQPTN

GVGYQPYRVVVLSFELLHAPATVCGPKKSTNLVKNKCVNF).
```

In certain embodiments, this disclosure relates to a peptide variant of SEQ ID NO: 1 having greater than 80%, 90%, 95%, 97%, 98% or 99% identity thereto. In certain embodiments, the peptide or variant contains a polyglycine and a polyhistidine on the C-terminus of SEQ ID NO: 1.

In certain embodiments this disclosure relates to a peptide comprising or consisting of SEQ

```
                                          SEQ ID NO: 2
(MFVFLVLLPLVSRVQPTESIVRFPNITNLCPFGEVENATRFASVYAWN

RKRISNCVADYSVLYNSASFSTFKCYGVSPTKLNDLCFTNVYADSFVIR
```

```
                             -continued
GDEVRQIAPGQTGKIADYNYKLPDDFTGCVIAWNSNNLDSKVGGNYNYL

YRLFRKSNLKPFERDISTEIYQAGSTPCNGVEGFNCYFPLQSYGFQPTN

GVGYQPYRVVVLSFELLHAPATVCGPKKSTNLVKNKCVNFGGGGSHHHH

HH).
```

In certain embodiments, this disclosure relates to a peptide variant of SEQ ID NO: 2 having greater than 80%, 90%, 95%, 97%, 98% or 99% identity thereto.

In certain embodiments, the peptide variant contains a N-terminus consisting of SEQ ID NO: 3 (MFVFLVLLPLVS) and the variant does not contain SEQ ID NO: 4 (GGGGSHHHHHH). In certain embodiments, the peptide variant does not contain SEQ ID NO: 4 (GGGGSHHHHHH). In certain embodiments, the peptide variant does not contain SEQ ID NO: 3 (MFVFLVLLPLVS). In certain embodiments, the peptide variant contains a C-terminus consisting of SEQ ID NO: 4 (GGGGSHHHHHH) and the variant does not contain SEQ ID NO: 3 (MFVFLVLLPLVS).

In certain embodiments, the peptide variant comprises one or more amino acid substitution within

```
                                          SEQ ID NO: 5
(RVQPTESIVRFPNITNLCPFGEVFNATRFASVYAWNRKRISNCVADYSV

LYNSASFSTFKCYGVSPTKLNDLCFTNVYADSFVIRGDEVRQIAPGQTGK

IADYNYKLPDDFTGCVIAWNSNNLDSKVGGNYNYLYRLFRKSNLKPFERD

ISTEIYQAGSTPCNGVEGFNCYFPLQSYGFQPTNGVGYQPYRVVVLSFEL

LHAPATVCGPKKSTNLVKNKCVNF).
```

In certain embodiments, the peptide has an N-terminus consisting of SEQ ID NO: 5 or variants thereof.

In certain embodiments, the peptide variant does not comprise one or more amino acid substitution within

```
                                          SEQ ID NO: 5
(RVQPTESIVRFPNITNLCPFGEVFNATRFASVYAWNRKRISNCVADYSV

LYNSASFSTFKCYGVSPTKLNDLCFTNVYADSFVIRGDEVRQIAPGQTGK

IADYNYKLPDDFTGCVIAWNSNNLDSKVGGNYNYLYRLFRKSNLKPFERD

ISTEIYQAGSTPCNGVEGFNCYFPLQSYGFQPTNGVGYQPYRVVVLSFEL

LHAPATVCGPKKSTNLVKNKCVNF).
```

In certain embodiments, the variant has greater than 80%, 90%, 95%, 97%, 98% or 99% identity to SEQ ID NO: 5.

The convention for referencing mutations positions for the coronavirus spike protein is associated with amino acid sequence

```
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV
```

-continued

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNF (SEQ ID

NO: 13) bold is (SEQ ID NO: 5).

In certain embodiments, the variant has a coronavirus spike protein variant selected from S477N, E484K or a combination thereof such as (SEQ ID NO: 14)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGNTPCNGVEGFNCYFPLQSYGFQPTNGVGYQPYRVVVLSFELL

HAPATVCGPKKSTNLVKNKCVNF
or (SEQ ID NO: 15)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVKGFNCYFPLQSYGFQPTNGVGYQPYRVVVLSFELL

HAPATVCGPKKSTNLVKNKCVNF.

In certain embodiments, the variant is L452R, (SEQ ID NO: 16)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNRYRLFRKSNLKPFERDI

STEIYQAGSTPCNGVEGFNCYFPLQSYGFQPTNGVGYQPYRVVVLSFELL

HAPATVCGPKKSTNLVKNKCVNF.

In certain embodiments, the variant is N501Y (SEQ ID NO: 17)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVEGFNCYFPLQSYGFQPTYGVGYQPYRVVVLSFELL

HAPATVCGPKKSTNLVKNKCVNF.

In certain embodiments, the variant is K417N (SEQ ID NO: 18)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGNI

-continued

ADYNYKLPDDFTGCVIAWNSNNLDSKVGGNYNYLYRLFRKSNLKPFERDI

STEIYQAGSTPCNGVEGFNCYFPLQSYGFQPTNGVGYQPYRVVVLSFELL

HAPATVCGPKKSTNLVKNKCVNF

In certain embodiments, the peptide or variant is conjugated to a solid surface, a particle, a magnetic particle, fluorescent particle, a fluorescent dye, or label.

In certain embodiments, this disclosure relates to fusion proteins comprising a peptide disclosed herein and a heterologous sequence.

In certain embodiments, this disclosure relates to vaccines comprising a peptide as disclosed herein or a nucleic acid encoding a peptide as disclosed herein. In certain embodiments, this disclosure relates to pharmaceutical composition comprising a peptide disclosed herein and a pharmaceutically acceptable excipient.

In certain embodiments, the disclosure contemplates peptides disclosed herein having at least one molecular modification, e.g., such that the peptide contains a non-naturally amino acid. In certain embodiments, the disclosure contemplates a non-naturally occurring derivative of a peptide disclosed herein. In certain embodiments, the disclosure contemplates a derivative in the form of a prodrug. In certain embodiments, the disclosure contemplates a derivative wherein an amino, carboxyl, hydroxyl, or thiol group in a peptide disclosed herein is substituted. In certain embodiments, the disclosure contemplates peptides disclosed herein having a label, e.g., fluorescent or radioactive.

In certain embodiments, the peptide is N-terminal substituted with a heterologous peptide. In certain embodiments, the peptide is C-terminal substituted with a heterologous peptide. In certain embodiments, the peptide is N-terminal substituted with an alkanoyl. In certain embodiments, alkanoyl is optionally substituted with a hydrophilic polymer such as polyethylene glycol. In certain embodiments, the peptide has C-terminal amide, wherein the amide is optionally substituted with alkyl. In certain embodiments, one or more carboxylic acid groups in the peptide are converted to alkyl esters such ethyl esters.

In certain embodiments, the peptides discloses herein have at least one non-naturally occurring molecular modification, such as the attachment of polyethylene glycol, the attachment of a heterologous peptide, the attachment of a fluorescent dye comprising aromatic groups, fluorescent peptide, a chelating agent capable of binding a radionuclide, N-terminal acetyl, propionyl group, myristoyl and palmitoyl, group or N-terminal methylation, or a C-terminal alkyl ester. In certain embodiments, the disclosure contemplates peptides disclosed herein labeled using biotinylation reagents (biotin, avidin, or streptavidin). Biotinylated peptides can be used in avidin/streptavidin affinity binding, purification, and detection. In certain embodiments, the disclosure contemplates peptides disclose herein containing azide-derivatives of naturally occurring monosaccharides such as N-azidoacetylglucosamine, N-azidoacetylmannosamine, and N-azidoacetylgalactosamine.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amine side chain group such as lysine or an amino acid containing a carboxylic acid side chain group such as aspartic acid or glutamic acid, within the peptide comprising a sequence disclosed herein. In certain embodiments, it is contemplated that the substituent may be covalently bonded through a cysteine in a sequence disclosed herein optionally connected through a linker. In certain embodiments, a substituent is connected through a linker that forms a disulfide with a cysteine amino acid side group.

In certain embodiments, the disclosure relates to recombinant vectors comprising a nucleic acid encoding peptide disclosed herein. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein. In certain embodiments, the disclosure relates to a vector comprising the nucleic acid encoding a peptide disclosed herein and a heterologous nucleic acid sequence.

In certain embodiments, the disclosure relates to a nucleic acid encoding a peptide disclosed herein wherein the nucleotide sequence has been changed to contain at least one non-naturally occurring substitution and/or modification relative to the naturally occurring sequence, e.g., one or more nucleotides have been changed relative to the natural sequence.

Methods of Use

In certain embodiments, this disclosure relates to methods of detecting the presence of a coronavirus in a sample comprising: contacting a sample with a peptide disclosed herein under conditions whereby the peptide acts as an antigen to form an antigen/antibody complex; and detecting formation of an antigen/antibody complex, whereby detection of formation of the antigen/antibody complex detects a coronavirus in the sample. In certain embodiments, a variety of assays can be employed for such detection. For example, various immunoassays can be used to detect antibodies or peptides disclosed herein as antigen. Such immunoassays typically involve the measurement of antigen/antibody complex formation between a peptide disclosed herein (i.e., as an antigen) and a coronavirus specific antibody.

A variety of immunoassay systems can be used, including but not limited to, radio-immunoassays (RIA), enzyme-linked immunosorbent assays (ELISA) assays, enzyme immunoassays (EIA), "sandwich" assays, focus reduction neutralization assays (FRNA), gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, immunoprecipitation, competitive binding assays, and immunohistochemical staining.

In certain embodiments, this disclosure relates to methods utilizing immunoassays that can be either competitive or noncompetitive. In competitive binding assays, an antigen (ACE2 receptor binding site on a surface spike protein of a coronavirus particle) competes with a detectably labeled peptide disclosed herein for specific binding to a capture site bound to a solid surface. The concentration of labeled peptide bound to the capture agent is inversely proportional to the amount of free ACE2 receptor binding site on a surface spike protein of a coronavirus particle present in the sample.

Noncompetitive assays, for example, sandwich assays, in which, for example, a peptide disclosed herein (i.e., as an antigen) is bound between two antibodies. One of the antibodies is used as a capture agent and is bound to a solid surface. The other antibody is labeled and is used to measure or detect the resultant a peptide disclosed herein (i.e., as an antigen)/antibody complex by e.g., visual or instrument means. A number of combinations of peptide disclosed herein (i.e., as an antigen) and antibody and labeled antibody constructs can be used.

In certain embodiments, the peptides disclosed herein (i.e., as an antigen) and unlabeled antibody complex can be detected by other proteins capable of specifically binding human immunoglobulin constant regions.

In certain embodiments, the non-competitive assays need not be sandwich assays. For instance, the coronavirus antibodies in the sample can be bound directly to a solid surface. The presence of coronavirus antibodies in the sample can then be detected using labeled peptides disclosed herein (i.e., as an antigen).

In some embodiments, peptides disclosed herein (i.e., as an antigen) can be conjugated or otherwise linked or connected (e.g., covalently or noncovalently) to a solid support (e.g., bead, plate, slide, dish, membrane or well). Peptides disclosed herein can also be conjugated or otherwise linked or connected to detectable groups such as radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein).

A variety of organic and inorganic polymers, both natural and synthetic can be used as the material for a solid surface. Nonlimiting examples of polymers include polyethylene, polypropylene, poly(4-methylbutene), polystyrene, polymethacrylate, poly(ethylene terephthalate), rayon, nylon, polyvinyl butyrate), polyvinylidene difluoride (PVDF), silicones, polyformaldehyde, cellulose, cellulose acetate, nitrocellulose, and the like. Other materials that can be used include, but are not limited to, paper, glass, ceramic, metal, metalloids, semi conductive materials, cements and the like. In addition, substances that form gels, such as proteins (e.g., gelatins), lipopolysaccharides, silicates, agarose and polyacrylamides can be used. Polymers that form several aqueous phases, such as dextran, polyalkylene glycol or surfactants, such as phospholipids, long chain (12-24 carbon atoms) alkyl ammonium salts and the like are also suitable. Where the solid surface is porous, various pore sizes can be employed depending upon the nature of the system.

In certain embodiments, methods disclosed can also be carried out using a variety of solid phase systems, as well as in a dry strip lateral flow system (e.g., a "dipstick" system) wherein a fluid sample is passes over the solid surface by capillary action, i.e., liquid is soaked up as spread over the absorbent substance (e.g., paper) comprising a peptide disclosed herein.

In certain embodiments, this disclosure relates to methods of measuring or quantifying whether a sample from a subject contains antibodies as a result of a coronavirus infection.

In certain embodiments, this disclosure relates to methods of measuring or quantifying whether a subject has antibodies, e.g., neutralizing antibodies, to coronavirus due to an infection comprising obtaining a sample from a subject infected with a coronavirus infection; contacting the sample with cells that expresses ACE2 on the cell membrane and an infectious coronavirus; culturing the cells; measuring and/or quantifying a reduction in virally-infected plaque or foci compared to a reference value or normalized value.

In certain embodiments, quantifying viral infectivity is by automated counting of plaques or foci. There are various types of plaques and foci that can be identified, e.g., using enzymatic or fluorescent labels or labeling with markers or proteins. Cells may be seeded and allowed to adhere to a surface forming multiple layers or monolayers. Coronavirus particles may be added to the surface for the purpose of measuring the infectivity. The coronavirus infected cell may lyse and/or spread the infection to adjacent cells where the infection cycle is repeated. If the infected cells are lysed an area will create a plaque (an area of infection surrounded by uninfected cells) which can be seen with an optical microscope or visually (e.g., by pouring off the overlay medium and adding a crystal violet solution until it has colored the cytoplasm, i.e., removing the excess solution reveals an uncolored location of dead cells) creating contrast between the cells and the opening. The samples are then imaged and analyzed using a cytometer to count the area of plaques.

Alternatively, immunostaining techniques using fluorescently labeled antibodies specific for a coronavirus spike protein (RBD antigen) may be used to detect infected host cells and infectious virus particles before an actual plaque is formed. A single or thin layer of cells that express ACE2 may be infected with various dilutions of the coronavirus. The cells and coronavirus are allowed to incubate for a period of time under an overlay medium that restricts the spread of infectious virus, creating localized clusters (foci) of infected cells. Areas are subsequently contacted with fluorescently labeled antibodies against the coronavirus spike protein (RBD antigen), and fluorescence microscopy may be used to count and quantify the number of foci.

In certain embodiments, this disclosure relates to methods of determining whether a subject contains neutralizing antibodies to coronavirus infection comprising obtaining a sample from a subject infected with a coronavirus infection; contacting the sample with cells that express ACE2 on the surface of the cells and an infectious coronavirus; culturing the cells; and measuring and/or quantifying a reduction in virally-infected plaques or foci compared to a reference value or normalized value thereby determining that the subject contains neutralizing antibodies.

In certain embodiments the subject from which a sample is obtained is at risk of or diagnosed with a coronavirus spike mutation/deletion selected from L5F, L18F, A67V, H69del, V70del, D80G, D80A, Y144del, F157S, T95I, D215G, L242del, A243del, L244del, D253G, K417N, S477N, E484K, L452R, F565L, D614G, Q677H, R682W, A701V, T791I, T859N, F888L, D950H, V1176F, or combinations thereof as in reference to the NCBI Reference Sequence: YP 009724390.1 for the surface glycoprotein for severe acute respiratory syndrome coronavirus 2, deletion at positions.

In certain embodiments, this disclosure relates to methods of determining whether a subject contains an effective amount of neutralizing antibodies to prevent death or organ failure from a coronavirus infection comprising obtaining a sample from a subject infected with a coronavirus infection; contacting the sample with cells that express ACE2 and a coronavirus; culturing the cells; measuring a reduction in virally-infected plaque or foci compared to a reference value or normalized value; and determining whether the subject has effective amount of neutralizing antibodies to recover, survive, prevent organ failure. In certain embodiments, if such a subject does not have an effective amount of neutralizing antibodies, then the subject is provided an aggressive coronavirus treatment such providing a blood transfusion from a patient that has recovered from a coronavirus infection because the subject has an effective amount of neutralizing antibodies, received an effective coronavirus vaccination, and/or is diagnosed with having an effective amount of neutralizing antibodies in the a blood product of the patient, e.g., using methods disclosed herein.

In certain embodiments, this disclosure relates to methods of determining whether a subject contains an effective amount of neutralizing antibodies to donate a blood product for a transfusion treatment comprising obtaining a sample from a subject infected or previously infected with a coronavirus infection; contacting the sample with cells that express ACE2 and a coronavirus; culturing the cells; and measuring and/or quantifying a reduction in virally-infected foci or plaques compared to a reference value, wherein if the measurement or quantity is below a threshold value determining that the subject qualifies as a blood product donor for coronavirus treatment.

In certain embodiments, this disclosure relates to methods of producing antibodies comprises administering a peptide disclosed herein to a subject in an effective amount to result in the production of antibodies and an isolating antibody producing cells from the subject.

In certain embodiments, this disclosure relates to methods of detecting coronavirus antibodies in a subject comprising contacting a sample from a subject containing a coronavirus antibody that specifically binds an receptor binding domain with a peptide disclosed herein and detecting binding of the antibody to the peptide thereby detecting a coronavirus antibody in the sample of the subject.

In certain embodiments, this disclosure relates to methods of detecting a coronavirus antibody comprising providing a solid surface coated with a peptide disclosed herein; contacting the solid surface with a sample from a subject suspected of having a coronavirus infection; wherein if the sample comprises an antibody that binds an expose epitope of the peptide, then a complex of the peptide and subject derived antibody is formed; contacting the complex with an immunoglobulin specific antibody conjugated to a label providing a second complex of a labeled immunoglobulin antibody and the subject derived antibody; detecting the second complex of a labeled immunoglobulin antibody and the subject derived antibody thereby detecting a coronavirus antibody in the sample of the subject.

In certain embodiments, peptides disclosed herein are used in methods of generating antibodies to the coronavirus ACE2 receptor binding domain (ACE2-RBD). In certain embodiments, the method comprises administering a peptide disclosed herein to a subject in an effective amount to result in the production of antibodies. In certain embodiments, the methods further comprise isolating antibody producing cells, e.g., plasma cells or B cells, wherein the antibodies bind the coronavirus receptor binding domain.

In certain embodiments, this disclosure relates to method of detecting antibodies being made against the receptor binding domain in a blood product of a subject. In certain embodiments, the methods indirectly detect for or test for a coronavirus infection through serologic testing whereby coronavirus antibodies in serum are being made by that individual against the receptor binding domain and are detected.

In certain embodiments, this disclosure relates to methods of detecting coronavirus antibodies in a subject comprising contacting a sample from a subject containing a coronavirus antibody that specifically binds a peptide disclosed herein with a peptide disclosed herein; and detecting binding of the antibody to the peptide indicating coronavirus antibodies in the sample or the subject. In certain embodiments, the peptide as disclosed herein is conjugated to or coated on a solid surface, a particle, magnetic particle, or a fluorescent particle. In certain embodiments, the peptide as disclosed herein is conjugated to a fluorescent dye, radioisotope, or label.

In certain embodiments, methods comprise providing a solid surface, e.g., a particle, glass container, microscope slide, tube, or a membrane, coated with a peptide disclosed herein or a specific binding agent e.g., anti-ACE2 RBD antibodies, bound to a peptide disclosed herein, thereby spatially fixing and coating a peptide disclosed herein, optionally conjugated or linked to a label, containing a coronavirus receptor binding domain to the solid surface; contacting the solid surface with a sample from a subject suspected of having a coronavirus infection; wherein if the sample comprises coronavirus antibodies that bind an expose epitope of fixed peptide disclosed herein, then the coronavirus antibodies bind to the fixed peptide disclosed herein providing a complex of peptides disclosed herein and subject derived coronavirus antibodies.

In certain embodiments, the methods further comprise contacting the surface comprising a complex of peptides disclosed herein and subject derived antibodies with secondary immunoglobulin specific antibodies conjugated to a label (anti-IgG antibodies, anti-IgM antibodies, and or anti-IgA antibodies).

In certain embodiments, the method further comprises detecting the label indicating the presence of coronavirus antibodies. In certain embodiments, the labeled secondary antibodies (e.g., labeled with a fluorescent agent, radiolabel, or an enzyme) binds subject derived antibodies exposed to the solid surface. If the labeled secondary antibodies are conjugated to a fluorescent dye or radiolabel (labeled with a radio isotope), the complex formed is proportional to the degree of fluorescence when viewed with a fluorescent microscope or device for detecting radioactivity. If the labeled secondary antibody contains an enzyme, one can add a substrate that produces a signal in the presence of the enzyme producing a signal proportional to the amount of enzyme-substrate reaction, e.g., a color change.

In certain embodiments, for any of the methods disclosed between any of the steps disclosed herein a washing step may be implemented to purify and/or separate the products from starting materials, reagents or byproducts.

In certain embodiments, this disclosure relates to methods of treating a coronavirus infection comprising administering to a subject in need thereof an effective amount of a blood product from a patient that has recovered from a prior coronavirus infection. In certain embodiments, a sample of the patient is measured for IgG and IgA providing measured levels of IgG and IgA; or wherein a sample of the patient is measured for IgG and IgM providing measured levels of IgG and IgM; wherein the blood product is selected from a patient wherein the measured levels of IgM are lower as compared to IgG; or wherein the blood product is selected from a patient wherein the measured levels of IgA are lower as compared to IgG.

In certain embodiments, the blood product from the patient is plasma. In certain embodiments, the subject to be treated is diagnosed with respiratory distress syndrome.

In certain embodiments, this disclosure relates to methods of treating a coronavirus infection comprising administering to a subject in need thereof an effective amount of a blood product from a patient immunized with a coronavirus vaccine. In certain embodiments, a sample of the patient is measured for IgG and IgA providing measured levels of IgG and IgA; or wherein a sample of the patient is measured for IgG and IgM providing measured levels of IgG and IgM; wherein the blood product is selected from a patient wherein the measured levels of IgM are lower as compared to IgG; or wherein the blood product is selected from a patient wherein the measured levels of IgA are lower as compared to IgG.

In certain embodiments, this disclosure relates to vaccination methods comprising administering an effective amount of a peptide disclosed herein to a subject optionally in combination with an adjuvant.

In certain embodiments, this disclosure relates to methods of determining immunization efficiency to a vaccine for a virus that causes respiratory distress syndrome comprising: administering a vaccine for a virus that causes respiratory distress syndrome to a subject; measuring IgG and IgM in a sample of the subject providing measured levels of IgG and IgM; or measuring IgG and IgA in a sample of the subject providing measured levels of IgG and IgA; diagnosing the subject as having an effective immunization if the measured levels of IgM are lower as compared to IgG; or diagnosing the subject as having an effective immunization if the measured levels of IgA are lower as compared to IgG.

In certain embodiments, any of the methods for measuring, detecting, or analyzing neutralizing antibodies as disclosed herein are performed after or only after 5, 6, or 7 days of having PCR confirmed infection. In certain embodiments, any of the methods for measuring, detecting, or analyzing neutralizing antibodies as disclosed herein are performed after or only after 5, 6, or 7 days of exhibiting symptoms (such as fever or respiratory distress) of a coronavirus infection. In certain embodiments, the coronavirus infection is a PCR confirmed infection.

Pharmaceutical and Vaccine Compositions

In certain embodiments, this disclosure relates to pharmaceutical or vaccine composition comprising peptides or nucleic acids encoding peptides disclosed herein and a pharmaceutically acceptable excipients such as stabilizers, preservatives, buffering agents, adjuvants, or antibiotics (e.g., neomycin, polymyxin B, streptomycin, gentamicin, thiomersal). In certain embodiments, the composition is in the form of a sterilized pH buffered aqueous salt solution or a saline phosphate buffer between a pH of 6 to 10 or an isotonic phosphate buffered saline solution, optionally comprising a saccharide or polysaccharide, such as sucrose and lactose, amino acids such as glycine or the monosodium salt of glutamic acid and proteins such as human serum albumin or gelatin.

In certain embodiments, a vaccine composition comprises an adjuvant such as aluminum hydroxide, aluminum phosphate, alum (potassium aluminum sulfate), monophosphoryl lipid A (MPL), aluminum hydroxide and monophosphoryl lipid A (MPL), D,L-alpha-tocopherol (vitamin E), squalene, D,L-alpha-tocopherol (vitamin E) and squalene.

In certain embodiments, the pharmaceutical composition is in the form of a tablet, pill, capsule, gel, gel capsule, or cream. In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

Rapid Generation of Neutralizing Antibody Responses in COVID-19 Patients

SARS-CoV-2, the virus responsible for COVID-19, is causing a devastating pandemic that has afflicted nearly every country throughout the world. There is a pressing need to understand the dynamics, specificity, and neutralizing potency of the humoral immune response during acute SARS-CoV-2 infection. The dynamics of the antibody response to the receptor-binding domain (RBD) of the spike protein and virus neutralization activity in a cohort of 44 acutely infected COVID-19 patients was investigated. RBD-specific IgG responses were detectable, yet varied by over two orders of magnitude, in all patients by day 6 after PCR confirmation. Isotype switching to IgG occurred rapidly and was made up exclusively of the IgG1 and IgG3 subclass, with little or no detectable IgG2 or IgG4. Using a clinical isolate of SARS-CoV-2, neutralizing antibody titers were detectable in all patients 6 days after PCR confirmation. Importantly, the magnitude of the RBD-specific IgG binding titers correlated strongly with the neutralizing potency of the patient samples. These findings were validated in a clinical setting where the initial analysis of the dynamics of RBD-specific IgG titers was corroborated in a much larger cohort of PCR-confirmed acute COVID-19 patient samples (n=231). These findings have important implications for understanding of protective immunity against SARS-CoV-2, the use of immune plasma as a therapeutic option, and the development of much-needed vaccines.

Experiments indicate that antibody responses to the spike (S) protein are the primary target of neutralizing activity during viral infection when compared to the membrane (M), envelope (E), and nucleocapsid proteins. The S glycoprotein is a class I viral fusion protein that exists as a metastable prefusion homotrimer consisting of individual polypeptide chains (between 1100-1600 residues in length) responsible for cell attachment and viral fusion. Each of the S protein protomers are divided into two distinct regions, the S1 and S2 subunits. The S1 subunit is a V-shaped polypeptide with four distinct domains, Domains A, B, C and D, with Domain B functioning as the receptor binding domain (RBD) for most coronaviruses, including the pathogenic β-coronaviruses such as SARS-CoV-2, SARS, and MERS. The SARS-CoV-2 RBD interacts with the ACE2 receptor for cellular attachment. Sequence analysis of the RBD shows extensive homology in this region to SARS (73%). In contrast, MERS and other seasonal coronaviruses show minimal sequence homology to the SARS-CoV-2 RBD (7-18%). Experiments were performed to evaluate the dynamics, specificity, and neutralizing potency of the humoral immune response against the RBD of the SARS-CoV-2 spike protein during acute infection.

Methods

CDC derived SARS-CoV-2 stain 2019-nCOV/USA_WA1/2020 was used. Viral titers were determined by plaque assay on Vero cells (ATCC). Vero cells were cultured in complete DMEM medium consisting of 1× DMEM, 10% FBS, 25 mM HEPES Buffer, 2 mM L-glutamine, 1 mM sodium pyruvate, 1× non-essential amino acids, and 1× antibiotics.

Cloning, Expression, and Purification of SARS-CoV-2 RDB

A recombinant form of the spike glycoprotein receptor binding domain (RBD) from SARS-CoV-2, Wuhan-Hu-1 (GenPept: QHD43416) was cloned for mammalian expression in human embryonic kidney expi293F cells. The receptor binding domain consisting of amino acids 319 (arginine) to 541 (phenylalanine)

```
                                    SEQ ID NO: 5
(RVQPTESIVRFPNITNLCPFGEVFNATRFASVYAWNRKRISNCVADYSV

LYNSASFSTFKCYGVSPTKLNDLCFTNVYADSFVIRGDEVRQIAPGQTGK

IADYNYKLPDDFTGCVIAWNSNNLDSKVGGNYNYLYRLFRKSNLKPFERD

ISTEIYQAGSTPCNGVEGFNCYFPLQSYGFQPTNGVGYQPYRVVVLSFEL

LHAPATVCGPKKSTNLVKNKCVNF)
``` of the SARS-Cov-2 S gene was amplified by PCR using a mammalian codon optimized sequence as the DNA template (Genscript MC_0101081).

PCR amplification appended the first 12 amino acids of the native S gene signal peptide sequence SEQ ID NO: 3 (MFVFLVLLPLVS) to the N-terminal end of the protein and at the C-terminal end a 6× polyhistidine tag preceded by a short linker sequence

```
                                    SEQ ID NO: 4
        (GGGGSHHHHHH).
```

Forward and Reverse primer sequences were:

```
                                    (SEQ ID NO: 7)
5'-AGAGAATTCACCATGTTCGTCTTCCTGGTCCTGCTGCCTCTGGTCTC

CAGGGTGCAGCCACCGAGTCTATC-3'
``` and

```
                                    (SEQ ID NO: 8)
5'-CTCTAAGCTTCTATCATTAGTGGTGGTGGTGGTGGTGGCTTCCGCCT

CCGCCGAAGTTCACGCACTTGTTCTTCAC-3'.
```

Twenty-five uL PCR reaction conditions were: 1× Phusion™ HF Buffer, 0.2 mM dNTP, 0.63 units Phusion™ DNA polymerase, and 500 nM of each primer. PCR cycling conditions: initial denaturation at 98° C., 1 minute; then 25 cycles of: 98° C., 20 seconds, 65° C. 30 seconds, 72° C. 30 seconds; followed a final extension at 72° C. for 5 minutes. Following amplification, purified PCR products were digested with EcoRI-HF and HindIII and cloned into the EcoRI-HindIII cloning site of a mammalian expression vector containing a CMV promoter (Genbank Reference ID FJ475055). Plasmid DNA was prepared using a purification system and constructs were sequence verified.

pCMV-SARS-nCOV2 RBD (SEQ ID NO: 6)

TTCGAGCTCGCCCGACATTGATTATTGACTAGTTATTAATAGTAATCAAT

TACGGGGTCATTAGTTCATAGCCCATATATGGAGTTCCGCGTTACATAAC

TTACGGTAAATGGCCCGCCTGGCTGACCGCCCAACGACCCCCGCCCATTG

ACGTCAATAATGACGTATGTTCCCATAGTAACGCCAATAGGGACTTTCCA

TTGACGTCAATGGGTGGAGTATTTACGGTAAACTGCCCACTTGGCAGTAC

ATCAAGTGTATCATATGCCAAGTACGCCCCCTATTGACGTCAATGACGGT

AAATGGCCCGCCTGGCATTATGCCCAGTACATGACCTTATGGGACTTTCC

TACTTGGCAGTACATCTACGTATTAGTCATCGCTATTACCATGGTGATGC

GGTTTTGGCAGTACATCAATGGGCGTGGATAGCGGTTTGACTCACGGGGA

TTTCCAAGTCTCCACCCCATTGACGTCAATGGGAGTTTGTTTTGGCACCA

AAATCAACGGGACTTTCCAAAATGTCGTAACAACTCCGCCCCATTGACGC

AAATGGGCGGTAGGCGTGTACGGTGGGAGGTCTATATAAGCAGAGCTCGT

TTAGTGAACCGTCAGATCGCCTGGAGACGCCATCCACGCTGTTTTGACCT

CCATAGAAGACACCGGGACCGATCCAGCCTCCGCGGCCGGGAACGGTGCA

TTGGAACGCGGATTCCCCGTGCCAAGAGTGACGTAAGTACCGCCTATAGA

GTCTATAGGCCCACCCCCTTGGCTTCGTTAGAACGCGGCTACAATTAATA

CATAACCTTATGTATCATACACATACGATTTAGGTGACACTATAGAATAA

CATCCACTTTGCCTTTCTCTCCACAGGTGTCCACTCCCAGGTCCAACTGC

ACCTCGGTTCTATCGATTGAATTCACCATGTTCGTCTTCCTGGTCCTGCT

GCCTCTGGTCTCCAGGGTGCAGCCAACCGAGTCTATCGTGCGCTTTCCTA

ATATCACAAACCTGTGCCCATTTGGCGAGGTGTTCAACGCAACCCGCTTC

GCCAGCGTGTACGCCTGGAATAGGAAGCGGATCAGCAACTGCGTGGCCGA

CTATAGCGTGCTGTACAACTCCGCCTCTTTCAGCACCTTTAAGTGCTATG

GCGTGTCCCCCACAAAGCTGAATGACCTGTGCTTTACCAACGTCTACGCC

GATTCTTTCGTGATCAGGGGCGACGAGGTGCGCCAGATCGCCCCCGGCCA

GACAGGCAAGATCGCAGACTACAATTATAAGCTGCCAGACGATTTCACCG

GCTGCGTGATCGCCTGGAACAGCAACAATCTGGATTCCAAAGTGGGCGGC

AACTACAATTATCTGTACCGGCTGTTTAGAAAGAGCAATCTGAAGCCCTT

CGAGAGGGACATCTCTACAGAAATCTACCAGGCCGGCAGCACCCCTTGCA

ATGGCGTGGAGGGCTTTAACTGTTATTTCCCACTCCAGTCCTACGGCTTC

CAGCCCACAAACGGCGTGGGCTATCAGCCTTACCGCGTGGTGGTGCTGAG

CTTTGAGCTGCTGCACGCCCCAGCAACAGTGTGCGGCCCCAAGAAGTCCA

CCAATCTGGTGAAGAACAAGTGCGTGAACTTCGGCGGAGGCGGAAGCCAC

CACCACCACCACCACTAATGATAGAAGCTTGGCCGCCATGGCCCAACTTG

TTTATTGCAGCTTATAATGGTTACAAATAAAGCAATAGCATCACAAATTT

CACAAATAAAGCATTTTTTTCACTGCATTCTAGTTGTGGTTTGTCCAAAC

TCATCAATGTATCTTATCATGTCTGGATCGGGAATTAATTCGGCGCAGCA

CCATGGCCTGAAATAACCTCTGAAAGAGGAACTTGGTTAGGTACCTTCTG

AGGCGGAAAGAACCATCTGTGGAATGTGTGTCAGTTAGGGTGTGGAAAGT

CCCCAGGCTCCCCAGCAGGCAGAAGTATGCAAAGCATGCATCTCAATTAG

-continued

TCAGCAACCAGGTGTGGAAAGTCCCCAGGCTCCCCAGCAGGCAGAAGTAT

GCAAAGCATGCATCTCAATTAGTCAGCAACCATAGTCCCGCCCCTAACTC

CGCCCATCCCGCCCCTAACTCCGCCCAGTTCCGCCCATTCTCCGCCCCAT

GGCTGACTAATTTTTTTTATTTATGCAGAGGCCGAGGCCGCCTCGGCCTC

TGAGCTATTCCAGAAGTAGTGAGGAGGCTTTTTTGGAGGCCTAGGCTTTT

GCAAAAAGCTGTTAACAGCTTGGCACTGGCCGTCGTTTTACAACGTCGTG

ACTGGGAAAACCCTGGCGTTACCCAACTTAATCGCCTTGCAGCACATCCC

CCTTTCGCCAGTTGGCGTAATAGCGAAGAGGCCCGCACCGATCGCCCTTC

CCAACAGTTGCGCAGCCTGAATGGCGAATGGCGCCTGATGCGGTATTTTC

TCCTTACGCATCTGTGCGGTATTTCACACCGCATACGTCAAAGCAACCAT

AGTACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGC

TTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTC

GACCCCAAAAAACTTGATTTGGGTGATGGTTCACGTAGTGGGCCATCGCC

CTGATAGACGGTTTTTCGCCCTTTGACGTTGGAGTCCACGTTCTTTAATA

GTGGACTCTTGTTCCAAACTGGAACAACACTCAACCCTATCTCGGGCTAT

TCTTTTGATTTATAAGGGATTTTGCCGATTTCGGCCTATTGGTTAAAAAA

TGAGCTGATTTAACAAAAATTTAACGCGAATTTTAACAAAATATTAACGT

TTACAATTTTATGGTGCACTCTCAGTACAATCTGCTCTGATGCCGCATAG

TTAAGCCAACTCCGCTATCGCTACGTGACTGGGTCATGGCTGCGCCCCGA

CACCCGCCAACACCCGCTGACGCGCCCTGACGGGCTTGTCTGCTCCCGGC

ATCCGCTTACAGACAAGCTGTGACCGTCTCCGGGAGCTGCATGTGTCAGA

GGTTTTCACCGTCATCACCGAAACGCGCGAGGCAGTATTCTTGAAGACGA

AAGGGCCTCGTGATACGCCTATTTTTATAGGTTAATGTCATGATAATAAT

GGTTTCTTAGACGTCAGGTGGCACTTTTCGGGGAAATGTGCGCGGAACCC

CTATTTGTTTATTTTTCTAAATACATTCAAATATGTATCCGCTCATGAGA

CAATAACCCTGATAAATGCTTCAATAATATTGAAAAAGGAAGAGTATGAG

TATTCAACATTTCCGTGTCGCCCTTATTCCCTTTTTTGCGGCATTTTGCC

TTCCTGTTTTTGCTCACCCAGAAACGCTGGTGAAAGTAAAAGATGCTGAA

GATCAGTTGGGTGCACGAGTGGGTTACATCGAACTGGATCTCAACAGCGG

TAAGATCCTTGAGAGTTTTCGCCCCGAAGAACGTTTTCCAATGATGAGCA

CTTTTAAAGTTCTGCTATGTGGCGCGGTATTATCCCGTGATGACGCCGGG

CAAGAGCAACTCGGTCGCCGCATACACTATTCTCAGAATGACTTGGTTGA

GTACTCACCAGTCACAGAAAAGCATCTTACGGATGGCATGACAGTAAGAG

AATTATGCAGTGCTGCCATAACCATGAGTGATAACACTGCGGCCAACTTA

CTTCTGACAACGATCGGAGGACCGAAGGAGCTAACCGCTTTTTTGCACAA

CATGGGGGATCATGTAACTCGCCTTGATCGTTGGGAACCGGAGCTGAATG

AAGCCATACCAAACGACGAGCGTGACACCACGATGCCTGTAGCAATGGCA

ACAACGTTGCGCAAACTATTAACTGGCGAACTACTTACTCTAGCTTCCCG

27

-continued

```
GCAACAATTAATAGACTGGATGGAGGCGGATAAAGTTGCAGGACCACTTC

TGCGCTCGGCCCTTCCGGCTGGCTGGTTTATTGCTGATAAATCTGGAGCC

GGTGAGCGTGGGTCTCGCGGTATCATTGCAGCACTGGGGCCAGATGGTAA

GCCCTCCCGTATCGTAGTTATCTACACGACGGGGAGTCAGGCAACTATGG

ATGAACGAAATAGACAGATCGCTGAGATAGGTGCCTCACTGATTAAGCAT

TGGTAACTGTCAGACCAAGTTTACTCATATATACTTTAGATTGATTTAAA

ACTTCATTTTTAATTTAAAAGGATCTAGGTGAAGATCCTTTTTGATAATC

TCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGT

AATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGC

AGAGCGCAGATACCAAATACTGTTCTTCTAGTGTAGCCGTAGTTAGGCCA

CCACTTCAAGAACTCTGTAGCACCGCCTACATACCTCGCTCTGCTAATCC

TGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGG

GGGTTCGTGCACACAGCCCAGCTTGGAGCGAACGACCTACACCGAACTGA

GATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGG

CGGAGCCTATGGAAAAACGCCAGCAACGCGGCCTTTTTACGGTTCCTGGC

CTTTTGCTGGCCTTTTGCTCACATGTTCTTTCCTGCGTTATCCCCTGATT

CTGTGGATAACCGTATTACCGCCTTTGAGTGAGCTGATACCGCTCGCCGC

AGCCGAACGACCGAGCGCAGCGAGTCAGTGAGCGAGGAAGCGGAAGAGCG

CCCAATACGCAAACCGCCTCTCCCCGCGCGTTGGCCGATTCATTAATCCA

GCTGGCACGACAGGTTTCCCGACTGGAAAGCGGGCAGTGAGCGCAACGCA

ATTAATGTGAGTTACCTCACTCATTAGGCACCCCAGGCTTTACACTTTAT

GCTTCCGGCTCGTATGTTGTGTGGAATTGTGAGCGGATAACAATTTCACA

CAGGAAACAGCTATGACCATGATTACGAATTAA
```

Recombinant protein expression was performed in Expi293F cells according to manufacturer's instructions. Briefly, expression plasmid DNA was complexed with a lipid-based transfection reagent. Complexes were added to the cell suspensions shaking at 125 RPM and incubated overnight at 37° C. in an 8% $CO_2$ humidified incubator. After 20 hours, protein expression supplements and antibiotics were added. Cultures were then incubated for an additional three days to allow for expression into the supernatant. Cell culture supernatants were harvested by centrifugation at 16,000×g for 10 minutes. Supernatants were sterile filtered through a 0.2 um filter and stored at 4° C. for less than 7 days before purification. Analytical SDS-PAGE was performed on supernatants and the protein concentration in solution was determined by densitometry relative to purified protein.

Recombinant RBD protein levels were between 100 mg and 150 mg per liter. Purification was performed using 5 mL HisTALON™ Superflow Cartridges. Briefly, an additional 11.7 g/L of sodium chloride and 0.71 g/L of cobalt (II) chloride hexahydrate were added to culture supernatants, which were adjusted to pH 7.5. The supernatant was then loaded on to the column equilibrated with 10 column volumes of 50 mM phosphate 300 mM sodium chloride buffer pH 7.5 (equilibration buffer). The column was washed with 8 column volumes of equilibration buffer supplemented with 10 mM imidazole. Protein was eluted with 6 column volumes of equilibration buffer supplemented with 150 mM imidazole. The eluted protein was dialyzed overnight against 80 volumes of phosphate buffered saline pH 7.2. The protein was filter sterilized (0.2 μm) and normalized to 1 mg/mL by UV spectrophotometry using an absorption coefficient of 1.3 AU at 280 nm=1 mg/mL. Proteins were aliquoted and stored at −80° C. prior to use. SDS-PAGE analysis of purified recombinant protein stained with coomassie blue demonstrated that samples were >90% pure. The RBD resolves at an apparent molecular weight of 30 kDa which is slightly larger than the theoretical molecular weight of 26.5 kDa, presumably caused by glycosylation.

Preparation of CR3022 Monoclonal Antibody and Biotinylation

The SARS-CoV S glycoprotein specific antibody CR3022 was generated recombinantly using previously reported heavy and light variable domain sequences deposited in GenBank under accession numbers DQ168569 and DQ16857011. Antibody variable domain gene sequences were synthesized and cloned into human IgG1 and human kappa expression vectors. Antibodies were produced in Expi293F cells according to manufactures recommendations by co-transfecting heavy and light chain plasmids at a ratio of 1:1.5. Antibodies were purified using rProtein A Sepharose Fast Flow™ antibody purification resin and buffer exchanged into PBS before use. Biotinylated versions of CR3022 used in viral neutralization assays were produced by combining the antibody with 20 molar excess of NHS-PEG4-Biotin for 1 hour at room temperatures. Reactions were stopped by adding Tris pH 8 to a final concentration of 10 mM. Biotinylated antibody was then buffer exchanged >1000× into PBS using a 10 kDa protein spin-concentrator.

Sequence Analysis and Alignment.

The SARS-CoV-2 spike protein structure was visualized in Pymol™. To assess homology of coronavirus spike proteins, a global protein alignment was performed in Geneious™ with translations of genome sequences accessed through NCBI Nucleotide. Sequences used were GenBank MN908947.3 (SARS-CoV-2), RefSeq NC_004718.3 (SARS-CoV), RefSeq NC 019843.3 (MERS-CoV), NC_006577.2 (HCoV—HKU1), RefSeq NC_006213.1 (HCoV—OC43), RefSeq NC_005831.2 (HCoV-NL63), and RefSeq NC_005831.2 (HCoV-229E). Homology at the RBD was determined by sequence identity between SARS-CoV-2 RBD residues T302 to L5606.

ELISA Assays

Recombinant SARS-CoV-2 RDB was coated on Nunc MaxiSorp™ plates at a concentration of 1 μg/mL in 100 μL phosphate buffered saline (PBS) at 4° C. overnight. Plates were blocked for two hours at room temperature in PBS/0.05% Tween/1% BSA (ELISA buffer). Serum or plasma samples were heated to 56° C. for 30 min, aliquoted, and stored at −20° C. before use. Samples were serially diluted 1:3 in dilution buffer (PBS-1% BSA-0.05% Tween-20) starting at a dilution of 1:100. 100 μL of each dilution was added and incubated for 90 minutes at room temperature. Horseradish peroxidase conjugated isotype (100 uL) and subclass specific secondary antibodies, diluted 1 to 2,000 in ELISA buffer, were added and incubated for 60 minutes at room temperature. Development was performed using 0.4 mg/mL o-phenylenediamine substrate in 0.05 M phosphate-citrate buffer pH 5.0, supplemented with 0.012% hydrogen peroxide before use. Reactions were stopped with 1 M HCl and absorbance was measured at 490 nm. Between each step, samples were washed four times with 300 μL of PBS-0.05% Tween. Prior to development, plates were additionally washed once with 300 μL of PBS. Secondary antibodies used for development were as follows: anti-hu-IgM-HRP, anti-hu-IgG-HRP, and anti-hu-IgA-HRP, and Mouse anti-hu-IgG1 Fc-HRP, Mouse anti-hu-IgG2 Fc-HRP, Mouse anti-hu-IgG3 Fc-HRP, or Mouse anti-hu-IgG4 Fc-HRP.

Clinical RBD ELISA Assay

This assay was performed as described above, with the following modifications to increase throughput: all serum samples were diluted 1:200, and the incubation times were reduced to 30 minutes after addition of serum samples and the secondary antibody conjugate.

Focus Reduction Neutralization Assays (FRNA)

Serially diluted patient plasma and COVID-19 (100-200 FFU) were combined in DMEM+1% FBS and incubated at 37° C. for 1 hour. The antibody-virus mixture was aliquoted on a monolayer of VeroE6 cells, gently rocked to distribute the mixture evenly, and incubated at 37° C. for 1 hour. After 1 hour, the antibody-virus inoculum was removed and prewarmed DMEM supplemented with 1% FBS, HEPES buffer, 2 mM L-glutamine, 1 mM sodium pyruvate, 1× Non-essential Amino Acids, 1× antibiotics (penicillin, strep-tomycin, amphotericin B) was mixed with methylcellulose (DMEM, 1% antibiotic, 2% FBS, 2% methylcellulose) at a 1:1 ratio and overlaid on the infected VeroE6 cell layer. Plates were incubated at 37° C. for 24 hours. After 24 hours, plates were gently washed three times with 1×PBS and fixed with 200 μl of 2% paraformaldehyde for 30 minutes. Following fixation, plates were washed twice with 1×PBS and 100 μl of permeabilization buffer (0.1% BSA-Saponin in PBS), was added to the fixated Vero cell monolayer for 20 minutes. Cells were incubated with an anti-SARS-CoV spike protein primary antibody conjugated to biotin (CR3022-biotin) for 1-2 hours at room temperature, then with avidin-HRP conjugated secondary antibody for 1 hour at room temperature. Foci were visualized using True Blue™ HRP substrate and imaged on an ELISPOT reader (CTL). Each plate contained three positive neutralization control wells, three negative control wells containing healthy control serum mixed with COVID-19, and three mock-infected wells.

Magnitude of RBD-Specific Antibody Responses in Acutely Infected COVID-19 Patients To determine the magnitude of antibody responses, Ig isotype, and IgG subclass usage against the RBD of the SARS-CoV-2 spike protein, a cohort of acutely infected COVID-19 patients (n=44) was analyzed. These patients were recruited from both the inpatient ward and the ICU. These samples represent a cross-section of days after patient-reported symptom onset (3-30 days) and PCR con-firmation (2-19 days). As healthy controls, plasma samples collected at baseline in a vaccine study performed in early 2019 (n=12) were used. The RBD protein was cloned and expressed in mammalian cells and was validated by ELISA using CR3022, a SARS-specific human monoclonal anti-body that cross-reacts with SARS-CoV-211 (FIG. 1A). Size exclusion chromatography shows that the recombinant RBD protein is homogenous and does not form aggregates (FIG. 1B). A majority of COVID-19 patients (36 out of 44) developed RBD-specific class-switched IgG responses (FIG. 1C) (mean titer: 18500, range: <100-142765). These patients also showed IgM and IgA responses of lower magnitude as compared to IgG (IgM mean titer: 3731, range: <100-40197 and IgA mean titer: 973, range: <100-19918). All of the negative controls were below the limit of detection in the endpoint analysis for binding to the RBD antigen (FIG. 1C). A number of the COVID-19 patient samples that scored either negative or low in the RBD IgG ELISA had higher titers of IgM. IgG subclass analysis showed that the COVID-19 patients exclusively made RBD-specific IgG1 and IgG3, with no detectable IgG2 or IgG4 (FIG. 1D). These results indicate that antibody class-switching to IgG occurs early during acute infection.

Neutralization Potency of Antibody Responses in COVID-19 Patients

Experiments were performed to determine the neutraliza-tion capacity of samples from the cohort of acutely infected COVID-19 patients. A focus reduction neutralization titer (FRNT) assay for SARS-CoV-2 was developed. In this assay, COVID-19 patient plasma is incubated with a clinical isolate of SARS-CoV-2 followed by infection of VeroE6 cells. The neutralization potency of the plasma sample is measured by the reduction in virally infected foci. Plasma from COVID-19 patients (n=44) was screened. A majority of the samples (40/44) showed neutralization capacity, with titers ranging from 1:5763 to 1:55 (FIG. 2A). A represen-tative example of viral neutralization is shown in FIG. 2B where pre-incubation with control plasma yields about 250 foci whereas the COVID-19 patient sample completely inhibited the formation of infected foci. Representative neutralization curves for a subset of samples are shown (FIG. 2C) to illustrate the dynamic range of the results obtained. A plaque reduction neutralization titer (PRNT) assay is the classic method for determining the neutraliza-tion capacity of a plasma sample against coronavirus infec-tion. To confirm the efficiency of these two assays, the neutralization titers between a standard PRNT assay and an FRNT assay was compared for a subset of the patient samples (n=9). Overall, a strong positive correlation between these two assays was observed (FIG. 2D), demon-strating the robustness of the FRNT assay. Overall, these findings indicate that neutralizing antibody responses are generated early during acute COVID-19 infection.

Kinetics of the Antibody Responses During Acute SARS-CoV-2 Infection

The patient samples were collected across a range of days after symptom onset or PCR confirmation of SARS-CoV-2 infection. To understand the relationship between these variables and RBD-specific IgG antibody titers and viral neutralization potency, correlation analyses were performed. Significant correlations were observed between the number of days elapsed after symptom onset or positive PCR test and the RBD-specific IgG titer or viral neutralization titer. Antibody responses against the RBD (FIG. 3A), as well as SARS-CoV-2 virus neutralization titers (FIG. 3B), can be detected in a majority of patients around day 8 after symp-tom onset. When the number of days after PCR confirmation is used to assess the duration of infection, both RBD-binding titers (FIG. 3C) and viral neutralization titers (FIG. 3D) can be detected in many patients already between days 2-6. Beyond 6 days post-PCR confirmation, all patients display both antibody binding and neutralization titers. Both RBD-specific and neutralizing antibody responses occur rapidly after SARS-CoV-2 infection.

RBD-Specific Antibody Titers as a Surrogate of Neutralization Potency in Acutely Infected COVID-19 Patients A wide range of RBD-specific and neutralizing antibody responses were observed across the cohort of acutely infected COVID-19 patients. The magnitude of RBD-specific IgG titers positively correlated with neutralization titers (FIG. 4A). Overall, viral neutralization activity in 40 out of 44 samples from acutely infected COVID-19 patients were observed.

RBD-specific IgG ELISA were validated for high-throughput testing. For these analyses, serums were collected from 231 PCR-confirmed COVID-19 patient samples within the first 22 days after PCR confirmation. In addition, 40 samples collected in 2019 were used as negative controls. These samples were grouped from 0-3 days, 4-6 days, and 7 or more days after PCR confirmation and analyzed using a high-throughput clinical RBD ELISA. The cumulative results of these efforts are shown as receiver operating characteristic (ROC) curves (FIG. 4B). This assay is almost perfectly discriminatory at day 7 or later after PCR confirmation, with an area under the curve (AUC) of 1.00 (n=83). When utilized earlier in the disease course, the performance of this diagnostic assay is reduced. When the RBD specific IgG ELISA were analyzed for the samples collected closer to the time of infection, the AUC for the day 4-6 group (n=76) and the day 0-3 group (n=72) fell to 0.93 and 0.80, respectively. Using an OD cut-off of 0.175 resulted in calculated sensitivity and specificity values of 97.5% and 98%, respectively. Taken together, these findings demonstrate that RBD-specific IgG titers could be used as a surrogate of neutralization activity against SARS-CoV-2 infection and that the RBD assay is highly specific and sensitive. Further, this demonstrates the necessity of appropriate timing of sample collection when using serologic diagnostic tests of acutely infected COVID-19 patients.

Neutralizing Antibodies Against SARS-CoV-2 Variants after Infection and Vaccination Serum neutralizing antibodies rapidly appear after SARS-CoV-2 infection and vaccination and are maintained for several months. The emergence of SARS-CoV-2 variants has raised concerns about the breadth of neutralizing-antibody responses. The neutralizing antibody response to 4 variants in infected and vaccinated individuals were compared to determine how mutations within the spike protein are associated with virus neutralization.

Live virus focus reduction neutralization tests (FRNTs) were performed. FRNT50 titers, which represent the reciprocal dilution of serum that neutralizes 50% of the input virus, were interpolated with a 4-parameter nonlinear regression, and geometric mean titers (GMTs) were calculated with 95% CI in GraphPad Prism version 8.4.3. Kruskal-Wallis test was used to compare FRNT50 GMTs between the variants. Comparison of the FRNT50 GMT of the variants was not statistically significant. This data indicates neutralizing activity of infection- and vaccine-elicited antibodies against 4 SARS-CoV-2 variants, including B.1, B.1.1.7, and N501Y. Because neutralization studies measure the ability of antibodies to block virus infection, these results suggest that infection- and vaccine-induced immunity may be retained against the B.1.1.7 variant.

Infection- and Vaccine-Induced Antibody Binding and Neutralization of the B.1.351 SARS-CoV-2 Variant Antibody binding and live virus neutralization of sera from naturally infected and Moderna vaccinated individuals were compared against two SARS-CoV-2 variants: B.1 containing the spike mutation D614G and the emerging B.1.351 variant containing additional spike mutations and deletions. Sera from acutely infected and convalescent COVID-19 patients exhibited a 3-fold reduction in binding antibody titers to the B.1.351 variant receptor-binding domain of the spike protein and a 3.5-fold reduction in neutralizing antibody titers against SARS-CoV-2 B.1.351 variant compared to the B.1 variant. Similar results were seen with sera from Moderna-vaccinated individuals. Despite reduced antibody titers against the B.1.351 variant, sera from infected and vaccinated individuals containing polyclonal antibodies to the spike protein could still neutralize SARS-CoV-2 B.1.351, suggesting that protective humoral immunity may be retained against this variant.

Mutations within the viral spike protein, in particular the receptor-binding domain (RBD), could influence viral binding and neutralization. The emerging B.1.351 SARS-CoV-2 variant includes three mutations within the receptor-binding domain (K417N, E484K, and N501Y) and several additional mutations within the spike protein. Two of these mutations are located at putative contact sites for the ACE2 receptor (amino acid positions 417 and 501). As it is possible that mutations within the spike protein can influence viral binding to the ACE2 receptor, antibody binding, and resistance to neutralization by human immune sera was evaluated.

Antibody binding and viral neutralization was evaluated against two variants that have emerged in various parts of the world. EHC-083E (herein referred to as the B. 1 variant) is within the B.1 PANGO lineage and was isolated from a residual nasopharyngeal swab collected from a patient (SARS-CoV-2/human/USA/GA-EHC-083E/2020). This variant contains the D614G mutation within the spike protein. The B.1.351 variant was isolated from an oropharyngeal swab from a patient South Africa. The B.1.351 viral variant contains the following amino acid mutations within the viral spike protein: L18F, D80A, D215G, deletion at positions 242-244 (L242del, A243del, and L244del), K417N, E484K, N501Y, and D614G. This virus was isolated and purified and followed by a single round of propagation in VeroE6 cells. Relative to the deposited sequence on GISAID (EPI_ISL_678615), two additional mutations within the spike protein at positions Q677H and R682W were identified.

A cohort of acutely infected COVID-19 patients (n=19) were analyzed between 5 and 19 days after symptom onset. As compared to the B.1-lineage, RBD-specific IgG responses (GMT: 4,829; range: <239-168,890), all of the patients had significantly reduced IgG binding to the B.1.351 RBD (GMT: 1,081; range: <239-20,254). The impact on the neutralization capacity of these samples using a live virus neutralization assay was determined. In comparison to the D614G variant (GMT: 135; range: <20-836), a significant reduction in the neutralization capacity of samples was observed from the acutely infected cohort against the B.1.351 variant (GMT: 40; range: <20-433). Of the samples that exhibited neutralization against the B.1 variant, 4/15 samples (26%) failed to neutralize the B.1.351 variant. While there was a range of RBD-specific and neutralizing antibody responses across this cohort of acutely infected COVID-19 patients, a positive correlation of the B.1-lineage RBD-specific IgG titers against the B.1 variant neutralization titers as well as the B.1.351 RBD-specific IgG titers against the B.1.351 variant neutralization titers was observed. These findings suggest that, during the acute phase of SARS-CoV-2 infection, mutations within the B.1.351 RBD account for the loss of neutralizing activity against the B.1.351 variant.

The messenger RNA vaccine mRNA-1273 generates durable neutralizing antibodies against SARS-CoV-2. Binding and neutralizing antibody titers in 19 healthy adult participants that received two injections of the mRNA-1273 vaccine at a dose of 100 µg (age >56 years; 14 days post-2nd dose) were examined. All vaccinated individuals had significantly reduced IgG binding to the B.1.351 RBD (GMT: 83,909; range: 2,588-333,451) compared to the B.1-lineage RBD-specific IgG responses (GMT: 316,554; range: 7,313-975,553). Similarly, a 3.8-fold reduction (p<0.0001) in neutralization capacity between the B.1. variant (GMT: 734;

range: 256-2,868) and the B.1.351 variant (GMT: 191; range: 61-830) was observed. In contrast to the infected individuals, all vaccinated individuals retained neutralization capacity against the B.1.351 variant. Further, a strong correlation between the corresponding RBD-specific IgG titers to the B.1 variant neutralization titers and the B.1.351 variant neutralization titers was observed. These findings demonstrate that the antibodies elicited by the mRNA-1273 vaccine are effective at neutralizing the B.1.351 variant.

What is claimed is:

1. A peptide comprising

```
                                    SEQ ID NO: 1
(MFVFLVLLPLVSRVQPTESIVRFPNITNLCPFGEVFNATRFASVYAWNR

KRISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYRL

FRKSNLKPFERDISTEIYQAGSTPCNGVEGFNCYFPLQSYGFQPTNGVGY

QPYRVVVLSFELLHAPATVCGPKKSTNLVKNKCVNF)
or
``` variant thereof with greater than 80% identity, wherein SEQ ID NO: 1 comprises a polyglycine and a polyhistidine on the C-terminus.

2. The peptide of claim 1 wherein a serine amino acid is between the polyglycine and the polyhistidine.

3. A peptide consisting of

```
                                    SEQ ID NO: 2
(MFVFLVLLPLVSRVQPTESIVRFPNITNLCPFGEVFNATRFASVYAWNR

KRISNCVADYSVLYNSASFSTFKCYGVSPTKLNDLCFTNVYADSFVIRGD

EVRQIAPGQTGKIADYNYKLPDDFTGCVIAWNSNNLDSKVGGNYNYLYRL

FRKSNLKPFERDISTEIYQAGSTPCNGVEGFNCYFPLQSYGFQPTNGVGY

QPYRVVVLSFELLHAPATVCGPKKSTNLVKNKCVNFGGGGSHHHHHH).
```

4. The peptide of claim 3 conjugated to or coated on a solid surface, a particle, magnetic particle, or a fluorescent particle.

5. The peptide of claim 3 conjugated to a fluorescent dye, radioisotope, or enzymatic label.

6. A pharmaceutical composition comprising a peptide of claim 3 and a pharmaceutically acceptable excipient.

7. A vaccination method comprising administering an effective amount of a peptide of claim 3 to a subject optionally in combination with an adjuvant.

8. A nucleic acid or vector encoding the peptide of claim 3 in operable combination with a heterologous promotor.

9. An expression system or cell comprising the nucleic acid or vector of claim 8.

10. A method of detecting coronavirus antibodies in a subject comprising contacting a sample from a subject containing a coronavirus antibody that specifically binds an ACE2 receptor binding domain with a peptide of claim 3; and detecting binding of the antibody to the peptide thereby detecting a coronavirus antibody in the sample of the subject.

11. The method of claim 10, wherein the subject is at risk of, exhibiting symptoms of, or diagnosed with a SARS-CoV-2 infection.

12. A method of detecting a coronavirus antibody comprising providing a solid surface coated with a peptide of claim 3;

contacting the solid surface with a sample from a subject suspected of having a coronavirus infection; wherein if the sample comprises an antibody that binds an expose epitope of the peptide, then a complex of the peptide and subject derived antibody is formed;

contacting the complex with an immunoglobulin specific antibody conjugated to a label providing a second complex of a labeled immunoglobulin antibody and the subject derived antibody;

detecting the second complex of a labeled immunoglobulin antibody and the subject derived antibody thereby detecting a coronavirus antibody in the sample of the subject.

\* \* \* \* \*

SEQUENCE LISTING

```
<160> NUMBER OF SEQ ID NOS: 18

<210> SEQ ID NO 1
<211> LENGTH: 235
<212> TYPE: PRT
<213> ORGANISM: Artificial
<220> FEATURE:
<223> OTHER INFORMATION: Synthetic construct

<400> SEQUENCE: 1

Met Phe Val Phe Leu Val Leu Leu Pro Leu Val Ser Arg Val Gln Pro
1               5                   10                  15

Thr Glu Ser Ile Val Arg Phe Pro Asn Ile Thr Asn Leu Cys Pro Phe
                20                  25                  30

Gly Glu Val Phe Asn Ala Thr Arg Phe Ala Ser Val Tyr Ala Trp Asn
            35                  40                  45

Arg Lys Arg Ile Ser Asn Cys Val Ala Asp Tyr Ser Val Leu Tyr Asn
        50                  55                  60

Ser Ala Ser Phe Ser Thr Phe Lys Cys Tyr Gly Val Ser Pro Thr Lys
65                  70                  75                  80

Leu Asn Asp Leu Cys Phe Thr Asn Val Tyr Ala Asp Ser Phe Val Ile
                85                  90                  95

Arg Gly Asp Glu Val Arg Gln Ile Ala Pro Gly Gln Thr Gly Lys Ile
            100                 105                 110

Ala Asp Tyr Asn Tyr Lys Leu Pro Asp Asp Phe Thr Gly Cys Val Ile
            115                 120                 125

Ala Trp Asn Ser Asn Asn Leu Asp Ser Lys Val Gly Gly Asn Tyr Asn
        130                 135                 140

Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
                165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Thr Asn Leu Val Lys Asn Lys Cys Val Asn Phe
225                 230                 235

<210> SEQ ID NO 2
<211> LENGTH: 246
<212> TYPE: PRT
<213> ORGANISM: Artificial
<220> FEATURE:
<223> OTHER INFORMATION: Synthetic construct

<400> SEQUENCE: 2
```

-continued

```
Met Phe Val Phe Leu Val Leu Leu Pro Leu Val Ser Arg Val Gln Pro
1               5                   10                  15

Thr Glu Ser Ile Val Arg Phe Pro Asn Ile Thr Asn Leu Cys Pro Phe
            20                  25                  30

Gly Glu Val Phe Asn Ala Thr Arg Phe Ala Ser Val Tyr Ala Trp Asn
        35                  40                  45

Arg Lys Arg Ile Ser Asn Cys Val Ala Asp Tyr Ser Val Leu Tyr Asn
    50                  55                  60

Ser Ala Ser Phe Ser Thr Phe Lys Cys Tyr Gly Val Ser Pro Thr Lys
65                  70                  75                  80

Leu Asn Asp Leu Cys Phe Thr Asn Val Tyr Ala Asp Ser Phe Val Ile
                85                  90                  95

Arg Gly Asp Glu Val Arg Gln Ile Ala Pro Gly Gln Thr Gly Lys Ile
            100                 105                 110

Ala Asp Tyr Asn Tyr Lys Leu Pro Asp Asp Phe Thr Gly Cys Val Ile
        115                 120                 125

Ala Trp Asn Ser Asn Asn Leu Asp Ser Lys Val Gly Gly Asn Tyr Asn
    130                 135                 140

Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
            165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Thr Asn Leu Val Lys Asn Lys Cys Val Asn Phe Gly Gly Gly Gly Ser
225                 230                 235                 240

His His His His His His
                245
```

```
<210> SEQ ID NO 3
<211> LENGTH: 12
<212> TYPE: PRT
<213> ORGANISM: Artificial
<220> FEATURE:
<223> OTHER INFORMATION: Synthetic construct

<400> SEQUENCE: 3

Met Phe Val Phe Leu Val Leu Leu Pro Leu Val Ser
1               5                   10

<210> SEQ ID NO 4
<211> LENGTH: 11
<212> TYPE: PRT
<213> ORGANISM: Artificial
<220> FEATURE:
<223> OTHER INFORMATION: Synthetic construct

<400> SEQUENCE: 4

Gly Gly Gly Gly Ser His His His His His
1               5                   10

<210> SEQ ID NO 5
<211> LENGTH: 223
<212> TYPE: PRT
<213> ORGANISM: Artificial
```

```
<220> FEATURE:
<223> OTHER INFORMATION: Synthetic construct

<400> SEQUENCE: 5

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe
    210                 215                 220

<210> SEQ ID NO 6
<211> LENGTH: 5433
<212> TYPE: DNA
<213> ORGANISM: Artificial
<220> FEATURE:
<223> OTHER INFORMATION: Synthetic construct

<400> SEQUENCE: 6
ttcgagctcg cccgacattg attattgact agttattaat agtaatcaat tacggggtca        60
ttagttcata gcccatatat ggagttccgc gttacataac ttacggtaaa tggcccgcct       120
ggctgaccgc ccaacgaccc ccgcccattg acgtcaataa tgacgtatgt tcccatagta       180
acgccaatag ggactttcca ttgacgtcaa tgggtggagt atttacggta aactgcccac       240
ttggcagtac atcaagtgta tcatatgcca gtacgcccc  ctattgacgt caatgacggt       300
aaatggcccg cctggcatta tgcccagtac atgaccttat gggactttcc tacttggcag       360
tacatctacg tattagtcat cgctattacc atggtgatgc ggttttggca gtacatcaat       420
gggcgtggat agcggtttga ctcacgggga tttccaagtc tccacccat  tgacgtcaat       480 gggagtttgt tttggcacca aaatcaacgg gactttccaa aatgtcgtaa caactccgcc       540
ccattgacgc aaatgggcgg taggcgtgta cggtgggagg tctatataag cagagctcgt       600
ttagtgaacc gtcagatcgc ctggagacgc catccacgct gttttgacct ccatagaaga       660
```

-continued

```
caccgggacc gatccagcct ccgcggccgg gaacggtgca ttggaacgcg gattccccgt        720
gccaagagtg acgtaagtac cgcctataga gtctataggc ccaccccctt ggcttcgtta        780
gaacgcggct acaattaata cataacctta tgtatcatac acatacgatt taggtgacac        840
tatagaataa catccacttt gcctttctct ccacaggtgt ccactcccag gtccaactgc        900
acctcggttc tatcgattga attcaccatg ttcgtcttcc tggtcctgct gcctctggtc        960
tccagggtgc agccaaccga gtctatcgtg cgctttccta atatcacaaa cctgtgccca       1020
tttggcgagg tgttcaacgc aacccgcttc gccagcgtgt acgcctggaa taggaagcgg       1080
atcagcaact gcgtggccga ctatagcgtg ctgtacaact ccgcctcttt cagcaccttt       1140
aagtgctatg gcgtgtcccc cacaaagctg aatgacctgt gctttaccaa cgtctacgcc       1200
gattctttcg tgatcagggg cgacgaggtg cgccagatcg cccccggcca gacaggcaag       1260
atcgcagact acaattataa gctgccagac gatttcaccg gctgcgtgat cgcctggaac       1320
agcaacaatc tggattccaa agtgggcggc aactacaatt atctgtaccg gctgtttaga       1380
aagagcaatc tgaagccctt cgagagggac atctctacag aaatctacca ggccggcagc       1440
accccttgca atggcgtgga gggctttaac tgttatttcc cactccagtc ctacggcttc       1500
cagcccacaa acggcgtggg ctatcagcct taccgcgtgg tggtgctgag ctttgagctg       1560
ctgcacgccc cagcaacagt gtgcggcccc aagaagtcca ccaatctggt gaagaacaag       1620
tgcgtgaact tcggcggagg cggaagccac caccaccacc accactaatg atagaagctt       1680
ggccgccatg gcccaacttg tttattgcag cttataatgg ttacaaataa agcaatagca       1740
tcacaaattt cacaaataaa gcattttttt cactgcattc tagttgtggt ttgtccaaac       1800
tcatcaatgt atcttatcat gtctggatcg ggaattaatt cggcgcagca ccatggcctg       1860
aaataacctc tgaaagagga acttggttag gtaccttctg aggcggaaag aaccatctgt       1920
ggaatgtgtg tcagttaggg tgtggaaagt ccccaggctc cccagcaggc agaagtatgc       1980
aaagcatgca tctcaattag tcagcaacca ggtgtggaaa gtccccaggc tccccagcag       2040
gcagaagtat gcaaagcatg catctcaatt agtcagcaac catagtcccg cccctaactc       2100
cgcccatccc gcccctaact ccgcccagtt ccgcccattc tccgccccat ggctgactaa       2160
ttttttttat ttatgcagag gccgaggccg cctcggcctc tgagctattc cagaagtagt       2220
gaggaggctt ttttggaggc ctaggctttt gcaaaaagct gttaacagct ggcactggc        2280 cgtcgtttta caacgtcgtg actgggaaaa ccctggcgtt acccaactta atcgccttgc       2340
agcacatccc cctttcgcca gttggcgtaa tagcgaagag gcccgcaccg atcgcccttc       2400
ccaacagttg cgcagcctga atggcgaatg gcgcctgatg cggtattttc tccttacgca       2460
tctgtgcggt atttcacacc gcatacgtca aagcaaccat agtacgcgcc ctgtagcggc       2520
gcattaagcg cggcgggtgt ggtggttacg cgcagcgtga ccgctacact tgccagcgcc       2580
ctagcgcccg ctcctttcgc tttcttccct tcctttctcg ccacgttcgc cggctttccc       2640
cgtcaagctc taaatcgggg gctcccttta gggttccgat ttagtgcttt acggcacctc       2700
gaccccaaaa aacttgattt gggtgatggt tcacgtagtg ggccatcgcc ctgatagacg       2760
gtttttcgcc ctttgacgtt ggagtccacg ttctttaata gtggactctt gttccaaact       2820
ggaacaacac tcaaccctat ctcgggctat tcttttgatt tataagggat tttgccgatt       2880
tcggcctatt ggttaaaaaa tgagctgatt taacaaaaat ttaacgcgaa ttttaacaaa       2940
atattaacgt ttacaatttt atggtgcact ctcagtacaa tctgctctga tgccgcatag       3000
ttaagccaac tccgctatcg ctacgtgact gggtcatggc tgcgccccga cacccgccaa       3060
```

-continued

```
caccegctga cgcgccctga cgggcttgtc tgctcccggc atccgcttac agacaagctg    3120
tgaccgtctc cgggagctgc atgtgtcaga ggttttcacc gtcatcaccg aaacgcgcga    3180
ggcagtattc ttgaagacga aagggcctcg tgatacgcct attttttatag gttaatgtca    3240 tgataataat ggtttcttag acgtcaggtg gcacttttcg gggaaatgtg cgcggaaccc    3300
ctatttgttt attttttctaa atacattcaa atatgtatcc gctcatgaga caataacccct    3360 gataaatgct tcaataatat tgaaaaagga agagtatgag tattcaacat ttccgtgtcg    3420
cccttattcc cttttttgcg gcattttgcc ttcctgtttt tgctcaccca gaaacgctgg    3480
tgaaagtaaa agatgctgaa gatcagttgg gtgcacgagt gggttacatc gaactggatc    3540
tcaacagcgg taagatcctt gagagttttc gccccgaaga acgttttcca atgatgagca    3600
cttttaaagt tctgctatgt ggcgcggtat tatcccgtga tgacgccggg caagagcaac    3660
tcggtcgccg catacactat tctcagaatg acttggttga gtactcacca gtcacagaaa    3720
agcatcttac ggatggcatg acagtaagag aattatgcag tgctgccata accatgagtg    3780
ataacactgc ggccaactta cttctgacaa cgatcggagg accgaaggag ctaaccgctt    3840
ttttgcacaa catgggggat catgtaactc gccttgatcg ttgggaaccg gagctgaatg    3900
aagccatacc aaacgacgag cgtgacacca cgatgcctgt agcaatggca acaacgttgc    3960
gcaaactatt aactggcgaa ctacttactc tagcttcccg gcaacaatta atagactgga    4020
tggaggcgga taaagttgca ggaccacttc tgcgctcggc ccttccggct ggctggttta    4080
ttgctgataa atctggagcc ggtgagcgtg ggtctcgcgg tatcattgca gcactggggc    4140
cagatggtaa gccctcccgt atcgtagtta tctacacgac ggggagtcag gcaactatgg    4200
atgaacgaaa tagacagatc gctgagatag gtgcctcact gattaagcat tggtaactgt    4260
cagaccaagt ttactcatat atactttaga ttgatttaaa acttcatttt taatttaaaa    4320
ggatctaggt gaagatcctt tttgataatc tcatgaccaa atcccttaa cgtgagtttt    4380 cgttccactg agcgtcagac cccgtagaaa agatcaaagg atcttcttga tccttttt    4440 ttctgcgcgt aatctgctgc ttgcaaacaa aaaaaccacc gctaccagcg gtggtttgtt    4500
tgccggatca agagctacca actctttttc cgaaggtaac tggcttcagc agagcgcaga    4560
taccaaatac tgttcttcta gtgtagccgt agttaggcca ccacttcaag aactctgtag    4620
caccgcctac atacctcgct ctgctaatcc tgttaccagt ggctgctgcc agtggcgata    4680
agtcgtgtct taccgggttg gactcaagac gatagttacc ggataaggcg cagcggtcgg    4740
gctgaacggg gggttcgtgc acacagccca gcttggagcg aacgacctac accgaactga    4800
gatacctaca gcgtgagcta tgagaaagcg ccacgcttcc cgaagggaga aaggcggaca    4860
ggtatccggt aagcggcagg gtcggaacag gagagcgcac gagggagctt ccagggggaa    4920
acgcctggta tctttatagt cctgtcgggt ttcgccacct ctgacttgag cgtcgatttt    4980
tgtgatgctc gtcaggggggg cggagcctat ggaaaaacgc cagcaacgcg gcctttttac    5040
ggttcctggc cttttgctgg ccttttgctc acatgttctt tcctgcgtta tcccctgatt    5100
ctgtggataa ccgtattacc gcctttgagt gagctgatac cgctcgccgc agccgaacga    5160
ccgagcgcag cgagtcagtg agcgaggaag cggaagagcg cccaatacgc aaaccgcctc    5220
tccccgcgcg ttggccgatt cattaatcca gctggcacga caggtttccc gactggaaag    5280
cgggcagtga gcgcaacgca attaatgtga gttacctcac tcattaggca ccccaggctt    5340
tacactttat gcttccggct cgtatgttgt gtggaattgt gagcggataa caatttcaca    5400
```
caggaaacag ctatgaccat gattacgaat taa                                        5433

<210> SEQ ID NO 7
<211> LENGTH: 71
<212> TYPE: DNA
<213> ORGANISM: Artificial
<220> FEATURE:
<223> OTHER INFORMATION: Synthetic construct

<400> SEQUENCE: 7
agagaattca ccatgttcgt cttcctggtc ctgctgcctc tggtctccag ggtgcagcca      60
ccgagtctat c                                                              71

<210> SEQ ID NO 8
<211> LENGTH: 76
<212> TYPE: DNA
<213> ORGANISM: Artificial
<220> FEATURE:
<223> OTHER INFORMATION: Synthetic construct

<400> SEQUENCE: 8
ctctaagctt ctatcattag tggtggtggt ggtggtggct ccgcctccg ccgaagttca      60 cgcacttgtt cttcac                                                         76

<210> SEQ ID NO 9
<211> LENGTH: 6
<212> TYPE: PRT
<213> ORGANISM: Artificial
<220> FEATURE:
<223> OTHER INFORMATION: Synthetic construct

<400> SEQUENCE: 9

Gly Gly Gly Gly Gly Gly
1               5

<210> SEQ ID NO 10
<211> LENGTH: 5
<212> TYPE: PRT
<213> ORGANISM: Artificial
<220> FEATURE:
<223> OTHER INFORMATION: Synthetic construct

<400> SEQUENCE: 10

Gly Gly Gly Gly Thr
1               5

<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Gly Gly Gly Pro Pro Pro
1               5

<210> SEQ ID NO 12
<211> LENGTH: 7
<212> TYPE: PRT
<213> ORGANISM: Artificial
<220> FEATURE:
<223> OTHER INFORMATION: Synthetic construct

<400> SEQUENCE: 12

-continued

```
Gly Gly Gly Ala Pro Pro Pro
1               5

<210> SEQ ID NO 13
<211> LENGTH: 541
<212> TYPE: PRT
<213> ORGANISM: Artificial
<220> FEATURE:
<223> OTHER INFORMATION: Synthetic construct

<400> SEQUENCE: 13

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350
```

-continued

```
Trp Asn Arg Lys Arg Ile Ser Asn Cys Val Ala Asp Tyr Ser Val Leu
        355             360             365

Tyr Asn Ser Ala Ser Phe Ser Thr Phe Lys Cys Tyr Gly Val Ser Pro
        370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
        450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe
        530             535             540

<210> SEQ ID NO 14
<211> LENGTH: 223
<212> TYPE: PRT
<213> ORGANISM: Artificial
<220> FEATURE:
<223> OTHER INFORMATION: Synthetic construct

<400> SEQUENCE: 14

Arg Val Gln Pro Thr Glu Ser Ile Val Arg Phe Pro Asn Ile Thr Asn
1               5               10              15

Leu Cys Pro Phe Gly Glu Val Phe Asn Ala Thr Arg Phe Ala Ser Val
            20              25              30

Tyr Ala Trp Asn Arg Lys Arg Ile Ser Asn Cys Val Ala Asp Tyr Ser
        35              40              45

Val Leu Tyr Asn Ser Ala Ser Phe Ser Thr Phe Lys Cys Tyr Gly Val
    50              55              60

Ser Pro Thr Lys Leu Asn Asp Leu Cys Phe Thr Asn Val Tyr Ala Asp
65              70              75              80

Ser Phe Val Ile Arg Gly Asp Glu Val Arg Gln Ile Ala Pro Gly Gln
                85              90              95

Thr Gly Lys Ile Ala Asp Tyr Asn Tyr Lys Leu Pro Asp Asp Phe Thr
            100             105             110

Gly Cys Val Ile Ala Trp Asn Ser Asn Asn Leu Asp Ser Lys Val Gly
            115             120             125

Gly Asn Tyr Asn Tyr Leu Tyr Arg Leu Phe Arg Lys Ser Asn Leu Lys
        130             135             140

Pro Phe Glu Arg Asp Ile Ser Thr Glu Ile Tyr Gln Ala Gly Asn Thr
145             150             155             160

Pro Cys Asn Gly Val Glu Gly Phe Asn Cys Tyr Phe Pro Leu Gln Ser
                165             170             175
```

-continued

```
Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220

<210> SEQ ID NO 15
<211> LENGTH: 223
<212> TYPE: PRT
<213> ORGANISM: Artificial
<220> FEATURE:
<223> OTHER INFORMATION: Synthetic construct

<400> SEQUENCE: 15

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
            85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Lys Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220

<210> SEQ ID NO 16
<211> LENGTH: 223
<212> TYPE: PRT
<213> ORGANISM: Artificial
<220> FEATURE:
<223> OTHER INFORMATION: Synthetic construct

<400> SEQUENCE: 16

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45
```

-continued

```
Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
            115                 120                 125

Gly Asn Tyr Asn Tyr Arg Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 17
<211> LENGTH: 223
<212> TYPE: PRT
<213> ORGANISM: Artificial
<220> FEATURE:
<223> OTHER INFORMATION: Synthetic construct

<400> SEQUENCE: 17

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
            165                 170                 175

Tyr Gly Phe Gln Pro Thr Tyr Gly Val Gly Tyr Gln Pro Tyr Arg Val
            180                 185                 190
```

-continued

```
Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
        210                 215                 220

<210> SEQ ID NO 18
<211> LENGTH: 223
<212> TYPE: PRT
<213> ORGANISM: Artificial
<220> FEATURE:
<223> OTHER INFORMATION: Synthetic construct

<400> SEQUENCE: 18

Arg Val Gln Pro Thr Glu Ser Ile Val Arg Phe Pro Asn Ile Thr Asn
1                 5                  10                  15

Leu Cys Pro Phe Gly Glu Val Phe Asn Ala Thr Arg Phe Ala Ser Val
        20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Asn Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
                180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
        210                 215                 220
```